(12) United States Patent
Chen et al.

(10) Patent No.: US 12,201,778 B2
(45) Date of Patent: Jan. 21, 2025

(54) WATER TANK MOUNTING STRUCTURE FOR VENTILATION TREATMENT APPARATUS AND VENTILATION TREATMENT APPARATUS

(71) Applicant: BMC (Tianjin) Medical Co., Ltd., Tianjin (CN)

(72) Inventors: Yunjing Chen, Tianjin (CN); Zhi Zhuang, Beijing (CN); Qingsong Wang, Beijing (CN); Fang Zheng, Tianjin (CN); Jian Xu, Beijing (CN)

(73) Assignee: BMC (Tianjin) Medical Co., Ltd., Tianjin (CN)

( * ) Notice: Subject to any disclaimer, the term of this patent is extended or adjusted under 35 U.S.C. 154(b) by 918 days.

(21) Appl. No.: 17/287,878

(22) PCT Filed: Oct. 25, 2019

(86) PCT No.: PCT/CN2019/113210
§ 371 (c)(1),
(2) Date: Apr. 22, 2021

(87) PCT Pub. No.: WO2020/083359
PCT Pub. Date: Apr. 30, 2020

(65) Prior Publication Data
US 2021/0372666 A1    Dec. 2, 2021

(30) Foreign Application Priority Data

Oct. 26, 2018 (CN) .......................... 201821757695.8
Oct. 26, 2018 (CN) .......................... 201821758281.7
Oct. 26, 2018 (CN) .......................... 201821763405.0

(51) Int. Cl.
*A61M 16/16* (2006.01)
*A61M 16/10* (2006.01)

(52) U.S. Cl.
CPC ............ *A61M 16/16* (2013.01); *A61M 16/10* (2013.01); *A61M 16/1075* (2013.01); *A61M 16/109* (2014.02)

(58) Field of Classification Search
CPC ............ A61M 16/0066; A61M 16/024; A61M 16/10–1095; A61M 16/125;
(Continued)

(56) References Cited

U.S. PATENT DOCUMENTS 4,993,411 A * 2/1991 Callaway .............. A61M 16/16
261/DIG. 65
10,004,871 B2 * 6/2018 Kat ....................... A61M 16/16
(Continued)

FOREIGN PATENT DOCUMENTS

CN    103800982 A    5/2014
CN    206081249 U    4/2017
(Continued)

OTHER PUBLICATIONS

KR 101795735 B1 translation accessed Mar. 13, 2024 (Year: 2024).*

*Primary Examiner* — Margaret M Luarca
*Assistant Examiner* — Kira B Daher
(74) *Attorney, Agent, or Firm* — Volpe Koenig

(57) ABSTRACT

A water tank mounting structure and a ventilation treatment apparatus for such structure. The water tank mounting structure comprises a cavity for containing a water tank and a side wall defining the cavity, wherein the side wall comprises an inner side wall spaced apart from an outer side, a first gas hole provided in the inner side wall, and a second gas hole provided in the outer side wall, both holes arranged in a staggered manner perpendicular to the side wall. The arrangement of the double-layer side wall, and the first and second gas holes in the inner and outer side walls, respec- (Continued)

tively, allows for hot gas in the cavity to be effectively removed. The staggered arrangement of the gas holes allows for water to flow downward along the side wall without invading the cavity when water enters through the second gas hole. A waterproof effect is achieved.

18 Claims, 35 Drawing Sheets

(58) Field of Classification Search
CPC ........ A61M 16/16–168; A61M 16/203; A61M 2016/0033; A61M 2016/102–1035; A61M 11/042; A61M 2202/0208; A61M 2205/362; A61M 2205/3334; A61M 2205/3606; A61M 2205/581; A61M 2205/587; A61M 2206/14; A62B 9/003; F24F 6/00–18
USPC .......................... 261/142; 128/204.11–204.29
See application file for complete search history.

(56) References Cited

U.S. PATENT DOCUMENTS

| | | | |
|---|---|---|---|
| 2003/0066526 A1* | 4/2003 | Thudor | A61M 16/161 128/203.26 |
| 2016/0108528 A1* | 4/2016 | Lin | A61M 16/101 204/278 |
| 2016/0206847 A1* | 7/2016 | Wang | A61M 16/16 |
| 2018/0110944 A1* | 4/2018 | Dai | A61M 16/16 |

FOREIGN PATENT DOCUMENTS

| | | |
|---|---|---|
| CN | 206285330 U | 6/2017 |
| CN | 209187818 U | 8/2019 |
| CN | 209237088 U | 8/2019 |
| GB | 2484076 A | 4/2012 |
| KR | 101795735 B1 * | 11/2017 |
| WO | 2010031126 A1 | 3/2010 |
| WO | 2016097928 A1 | 6/2016 |
| WO | 2016150373 A1 | 9/2016 |

* cited by examiner

WATER TANK MOUNTING STRUCTURE FOR VENTILATION TREATMENT APPARATUS AND VENTILATION TREATMENT APPARATUS

CROSS REFERENCE TO RELATED APPLICATIONS

This application is a 35 USC § 371 National Stage application of International Patent Application No. PCT/CN2019/113210, which was filed Oct. 25, 2019, entitled "WATER TANK MOUNTING STRUCTURE FOR VENTILATION TREATMENT APPARATUS AND VENTILATION TREATMENT APPARATUS," and claims priority to Chinese Patent Application No. 201821758281.7, filed Oct. 26, 2018, Chinese Patent Application No. 201821757695.8, filed Oct. 26, 2018 and Chinese Patent Application No. 201821763405.0, filed Oct. 26, 2018, all of which are incorporated herein by reference as if fully set forth.

FIELD

The present invention relates to the field of ventilation treatment, in particular to a water tank mounting structure for a ventilation treatment apparatus and a ventilation treatment apparatus including the water tank mounting structure.

BACKGROUND

Presently, ventilation treatment apparatuses, such as respirators, usually are equipped with a humidifying device to increase the humidity of the inhaled gas. By warming and humidifying the gas flow through the humidifying device, the adverse effects caused by mycteroxerosis (e.g., nasal obstruction and nasal bleeding, etc.) can be reduced, and the resistance in the nasal cavity can be decreased, the stability of the pressure in the respiratory mask can be ensured effectively, thereby the treatment effect and adaptability of the ventilation treatment apparatuses can be improved.

The humidifying device usually comprises a water tank that serves as a water source and a heating assembly capable of heating the water in the water tank, wherein the water tank is usually mounted in a cavity of the humidifying device. However, in the existing humidifying devices, the cavity is an airtight structure, the gas temperature in the cavity will be increased as the heating assembly carries out heating continuously, and the hot gas in the cavity can't be vented; moreover, since the side wall for defining the cavity is a single-layer structure, the foreign substances or water in the external environment may enter into the cavity easily and affect the use of the ventilation treatment apparatus if gas holes are arranged in the side wall simply.

SUMMARY

The present invention is intended to provide a water tank mounting structure for a ventilation treatment apparatus and a ventilation treatment apparatus including the water tank mounting structure, so as to solve the above problems.

To attain the objects described above, in one aspect, the present invention provides a water tank mounting structure for a ventilation treatment apparatus, comprising a cavity for containing a water tank and a side wall for defining the cavity, wherein the side wall comprises an inner side wall and an outer side wall spaced apart from each other, a first gas hole is provided in the inner side wall, a second gas hole is provided in the outer side wall, and the first gas hole and the second gas hole are arranged in a staggered manner in a direction perpendicular to the side wall.

According to the water tank mounting structure provided by the present invention, by using a double-layer side wall to define the cavity for containing the water tank, and providing the first gas hole and the second gas hole respectively in the inner side wall and the outer side wall, hot gas in the cavity can be effectively removed; besides, by arranging the first gas hole and the second gas hole in a staggered manner, when external water enters through the second gas hole, the water flows downward along the side wall without invading into the cavity, thus a waterproof effect is achieved.

Optionally, a plurality of first gas holes are provided in the inner side wall, spaced apart from each other in the height direction of the inner side wall, and arranged in rows in the width direction of the inner side wall.

Optionally, a plurality of second gas holes are provided in the outer side wall, spaced apart from each other in the height direction of the outer side wall, and arranged in rows in the width direction of the outer side wall.

In that way, a plurality of first gas holes and a plurality of second gas holes are provided in the water tank mounting structure in the present invention, so as to improve the gas permeability of the cavity.

Optionally, the inner side wall is parallel to the outer side wall. Thus, the manufacturing cost of the side wall can be reduced, the appearance of the product is more attractive, and the water entering into the space between the outer side wall and the inner side wall can flow downward to the bottom of the side wall more easily.

Optionally, the water tank mounting structure comprises a guide channel arranged on the bottom of the side wall for guiding out the water between the outer side wall and the inner side wall. By providing the guide channel, the water flowing to the bottom of the side wall can be drained off timely.

Optionally, the water tank mounting structure comprises a bottom plate extending inward from the bottom of the outer side wall and a stop rib spaced apart from the outer side wall and extending upward from the bottom plate, the stop rib is located on the inner side of the inner side wall, and the guide channel is defined by the outer side wall, the bottom plate, and the stop rib; or the water tank mounting structure comprises a bottom plate connected between the outer side wall and the inner side wall, and the guide channel is defined by the outer side wall, the inner side wall and the bottom plate, wherein the bottom plate is provided with a drain port.

Optionally, the water tank mounting structure comprises a top wall for defining the cavity, and the top wall comprises an inner top wall and an outer top wall that are spaced apart from each other. By configuring the top wall as a double-layer structure, the strength of the water tank mounting structure be strengthened, and other functional components can be arranged on the top wall, so as to improve the use of the ventilation treatment apparatus and optimize the structure of the ventilation treatment apparatus.

Optionally, an illuminating component for illuminating the cavity is provided on the inner top wall.

Optionally, a wiring groove is provided in the top surface of the inner top wall.

Optionally, the water tank mounting structure comprises a bottom wall for defining the cavity, a base located below the bottom wall and a heating plate, wherein the bottom wall is provided with an opening for containing the heating plate, and the base is provided with a supporting component for supporting the heating plate at the opening. Thus, the water in the water tank can be heated.

Optionally, the supporting component comprises a supporting column extending upward from a top surface of the base, and a spring sleeved on the supporting column with a top end abutting against a bottom surface of the heating plate. Thus, the spring can force the heating plate to adhere to the bottom of the water tank, so as to improve the heating efficiency and attain a shockproof effect.

Optionally, the water tank mounting structure comprises a back wall for defining the cavity, with an opening for mounting an intake tube of the ventilation treatment apparatus is arranged in the rear wall, and the water tank mounting structure comprises a guiding assembly for guiding the water tank to assemble to the cavity in a way that the gas inlet of the water tank is aligned to the opening.

According to the water tank mounting structure provided by the present invention, by arranging the guiding assembly, the gas inlet of the water tank can be aligned to the opening for mounting the intake tube while the water tank is guided to assemble to the cavity, so as to facilitate the mounting of the water tank of the water tank mounting structure as well as ensure the airtightness of the water tank.

Optionally, the water tank comprises a main body and an adapter connected above the main body, wherein the adapter comprises a horizontal tube extending in a horizontal assembling direction of the water tank, and an end of the horizontal tube oriented to the back wall is the gas inlet.

Optionally, the guiding assembly comprises a first guiding component to be fitted with the horizontal tube to guide the assembling of the water tank and/or a second guiding component to be fitted with the main body to guide the assembling of the water tank.

Optionally, the water tank mounting structure comprises a top wall for defining the cavity, the first guiding component comprises two guiding plates protruding downward from the top wall and extending in the assembling direction, the two guiding plates are located at two sides of the opening in a spaced manner in a direction perpendicular to the assembling direction, and horizontal tube is able to enter into the spacing between the two guiding plates.

Optionally, a guiding bevel is formed on an end of the guiding plate away from the opening. The arrangement of the guiding bevel can facilitate the horizontal tube to smoothly enter into the space between the two guiding plates during the assembling.

Optionally, the water tank mounting structure comprises a positioning structure for positioning the water tank in its assembling direction. By arranging the positioning structure, the reliability of mounting of the water tank can be improved, and gas leakage caused by the swaying of the water tank in the cavity or the loosening of other connecting components can be avoided.

Optionally, the positioning structure comprises a flange arranged on one of an inner side of the guiding plate and an outer wall of the horizontal tube, and a groove arranged on the other of the inner side of the guiding plate and the outer wall of the horizontal tube to be fitted with the flange. By utilizing the positioning structure that employs flange and groove fitting, the water tank mounting structure has a simpler structure and reduced manufacturing cost, and effective positioning of the water tank is ensured.

Optionally, the water tank mounting structure comprises two side walls arranged opposite to each other, the second guiding component comprises two guide rails arranged on the two side walls respectively, and the main body is provided with a sliding part that is able to be fitted with the two guide rails and slide along the two guide rails.

Optionally, the cross section of the main body is circular, the sliding part is an annular convex edge protruding outward from an outer circumferential surface of the main body and extending in the circumferential direction of the main body, the guide rails comprise two guiding ribs that protrude from an inner surface of the side wall and extend in the assembling direction, and the two guiding ribs have an interval in the height direction of the side wall, and the interval is set to allow the annular convex edge to enter.

Optionally, the spacing between the two guide rails is decreased in the assembling direction to prevent the main body to move further in the assembling direction after it reaches the assembling position.

In another aspect, the present invention provides a ventilation treatment apparatus, which comprises a main unit, a water tank, and the water tank mounting structure described above, wherein the water tank mounting structure is arranged on the main unit.

Optionally, the ventilation treatment apparatus comprises a casing and an oxygen assembly, wherein a main unit cavity is defined in the casing, and a partition assembly is arranged in the main unit cavity, the partition assembly separates an airtight oxygen isolation chamber in the main unit cavity, and the oxygen assembly is mounted in the oxygen isolation chamber.

According to the ventilation treatment apparatus provided by the present invention, by arranging a partition assembly in the main unit cavity to separate an oxygen isolation chamber and mounting the oxygen assembly in the oxygen isolation chamber, the oxygen assembly is isolated from the electronic components such as circuit boards, etc. Thus, once the oxygen leaks, it will not diffuse into other areas of the main unit cavity immediately; instead, the oxygen will be contained in the separate oxygen isolation chamber. Thereby the reliability and safety of the ventilation treatment apparatus are improved.

Optionally, the partition assembly is configured to separate a fan chamber in the main unit cavity, the casing comprises a top wall and a bottom wall for defining the main unit cavity, the partition assembly comprises an upper partition that comprises bottom plates arranged above the bottom wall in a spaced manner, the bottom plates separate the main unit cavity into an upper cavity and a lower cavity, the oxygen isolation chamber is located in the upper cavity, and the fan chamber is located in the lower cavity. By arranging the fan chamber for mounting the fan assembly in the lower cavity, the center of gravity of the entire apparatus is low, and thereby the stability of placement of the apparatus is improved.

Optionally, a power supply chamber is arranged in the main unit cavity, the partition assembly further comprises an upper side plate that extends from the bottom plates upward to the top wall and separates the upper cavity into a left cavity and a right cavity, and the oxygen isolation chamber and the power supply chamber are located in either of the left cavity and the right cavity respectively.

Optionally, the casing comprises a back wall, a left side wall and a right side wall for defining the main unit cavity, the oxygen isolation chamber is defined by the top wall, the bottom plates, the left side wall and the upper side plate, and the power supply chamber is defined by the top wall, the bottom plates, the right side wall and the upper side plate.

Optionally, the partition assembly comprises a lower partition that extends from the bottom wall upward to the bottom plates and is connected to the bottom plates by means of a snap-fit structure, and the lower partition comprises a plurality of lower side plates that enclose with each other to define the fan chamber in the lower cavity.

Optionally, the main unit cavity comprises a main board mounting chamber located at the front side of the upper cavity and the lower cavity, the casing comprises a panel for defining the main unit cavity, and the main board mounting chamber is defined by the top wall, the bottom wall, the left side wall, the right side wall, the panel, the upper side plate, and the lower side plate.

Optionally, the ventilation treatment apparatus comprises a fan assembly mounted in the fan chamber, the fan assembly comprises a fan housing and a fan, an oxygen mixing compartment and a fan compartment for mounting the fan are defined in the fan housing, the fan housing is provided with a gas inlet communicating with the fan compartment and a gas outlet communicating with the fan compartment and the oxygen mixing compartment, and the fan housing is further provided with an oxygen inlet and a mixed gas outlet that communicate with the oxygen mixing compartment.

Optionally, the fan assembly comprises a baffle arranged in the oxygen mixing compartment and configured to mix the gas and guide the gas to flow, a first measuring component for measuring the oxygen flow at the oxygen inlet, and a second measuring component for measuring the oxygen concentration at the mixed gas outlet.

Optionally, the oxygen assembly comprises an oxygen connector, an oxygen proportioning valve, a first tube and a second tube, wherein the first tube communicates with the oxygen connector and the oxygen proportioning valve, and the second tube communicates with the oxygen proportioning valve and the oxygen inlet. In case there is any leakage at the joints between the oxygen connector, the oxygen proportioning valve, the first tube and the second tube, the leaking oxygen will not invade into other areas of the main unit cavity since these components are enclosed in the oxygen isolation chamber.

Optionally, a ventilating fan is provided in the oxygen isolation chamber. In case of oxygen leakage, the oxygen can be vented quickly by means of the ventilating fan, so as to decrease the oxygen concentration.

Other features and advantages of the present invention will be further detailed in the embodiments hereunder.

BRIEF DESCRIPTION OF THE DRAWINGS

The accompanying drawings are provided here to facilitate further understanding on the present invention, and constitute a part of this document. They are used in conjunction with the following embodiments to explain the present invention, but shall not be comprehended as constituting any limitation to the present invention. In the figures.

REFERENCE NUMBERS

10—main unit; 11—cavity; 12—back wall; 121—opening; 122—limiting rib; 13—inner top wall; 131—guiding plate; 132—guiding bevel; 133—flange; 134—LED lamp; 135—wiring groove; 14—inner side wall; 141—guide rail; 142—mounting slot; 143—first gas hole; 15—bottom wall; 16—intake tube; 17—sealing element; 18—heating tube connector; 20—water tank; 21—main body; 211—annular convex edge; 212—first interface; 213—second interface; 22—adapter; 221—horizontal tube; 222—gas inlet; 223—groove; 224—vertical tube; 225—third interface; 226—fourth interface; 227—gas outlet; 228—check valve; 23—water injection tube; 30—casing; 31—outer top wall; 311—notch; 32—outer side wall; 321—second gas hole; 33—bottom plate; 331—stop rib; 34—base; 341—supporting column; 342—spring; 35—heating plate; 36—front cover; 410—casing; 4101—top wall; 4102—bottom wall; 4103—back wall; 4104—left side wall; 4105—right side wall; 4106—panel; 4107—second fitting surface; 411—upper partition; 4111—bottom plate; 4112—upper side plate; 412—lower partition; 4121—lower side plate; 413—oxygen isolation chamber; 4131—mounting hole; 414—fan chamber; 415—power supply chamber; 416—main board mounting chamber; 417—ventilating fan; 418—humidifying cavity; 420—oxygen assembly; 421—oxygen connector; 422—oxygen proportioning valve; 423—first tube; 424—second tube; 425—oxygen pressure sensor; 426—bracket; 430—fan assembly; 431—fan housing; 4311—gas inlet; 4312—gas outlet; 4313—communicating port; 4314—oxygen inlet; 4315—mixed gas outlet; 4316—upper fan housing; 4317—lower fan housing; 432—oxygen mixing compartment; 4321—baffle; 4322—first measuring component; 4323—second measuring component; 433—first fan compartment; 434—second fan compartment; 435—first fan; 4351—positioning ring; 4352—main body of fan; 4353—supporting component; 436—second fan; 437—connecting tube; 440—main board; 4401—main board screen; 4402—control key; 441—acrylic plate; 4411—knob mounting hole; 4412—button mounting hole; 442—light guiding base; 4421—claw; 4422—positioning post; 4423—first fitting surface; 443—seal ring; 444—knob; 445—button; 446—silicone button pad; 4461—upper fitting surface; 4462—middle fitting surface; 4463—lower fitting surface; 4464—groove.

DETAILED DESCRIPTION

Hereunder some embodiments of the present invention will be detailed with reference to the accompanying drawings. It should be understood that the embodiments described herein are only provided to describe and explain the present invention rather than constitute any limitation to the present invention.

Figure 1:
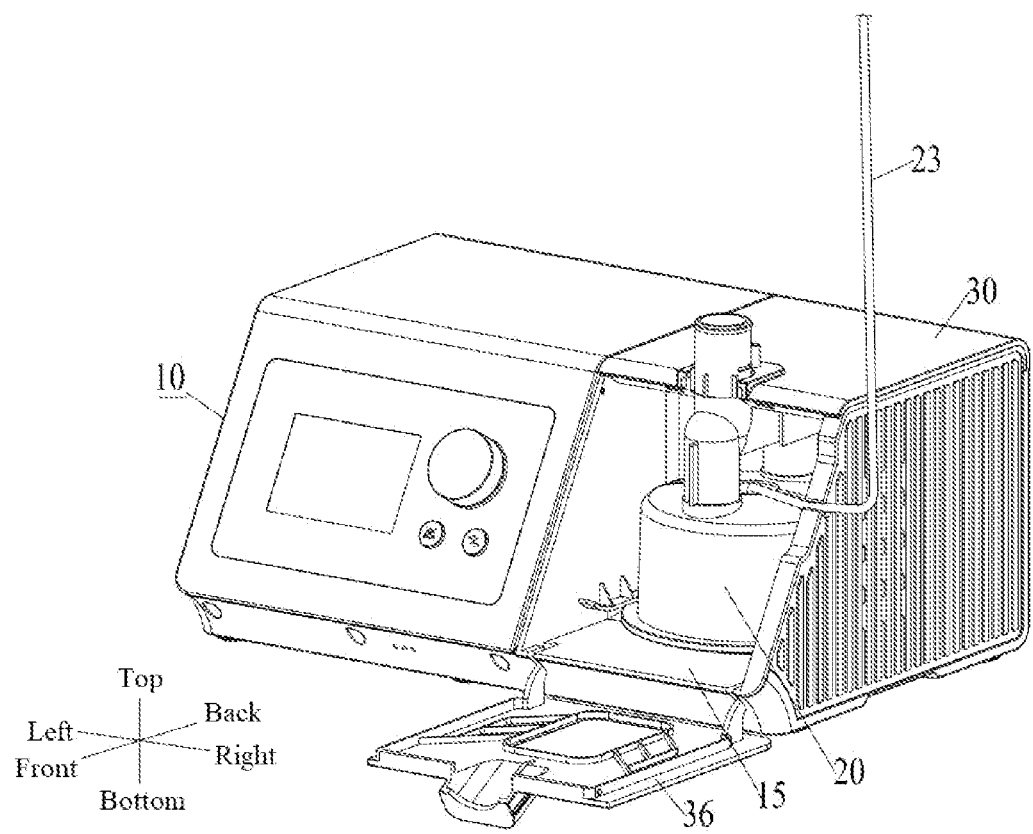
FIG. 1 is a schematic structural diagram of an embodiment of the ventilation treatment apparatus in the present invention.

Unless otherwise specified in the present invention, the terms that denotes the directions or orientations, such as "top", "bottom", "front", "back", "left", "right", etc., usually refer to the directions or orientations as indicated in FIG. 1; "inside" and "outside" usually refers to inside and outside with respect to the outlines of the components.

In ventilation treatment apparatuses, the humidifying device usually includes a heating assembly capable of heating the water in the water tank. However, in the existing humidifying devices, the cavity is an airtight structure, the gas temperature in the cavity will be increased as the heating assembly carries out heating continuously, and the hot gas in the cavity can't be vented; moreover, since the side wall for defining the cavity is a single-layer structure, the foreign substances or water in the external environment may enter into the cavity easily and affect the use of the ventilation treatment apparatus if gas holes are arranged in the side wall simply.

Figure 3:
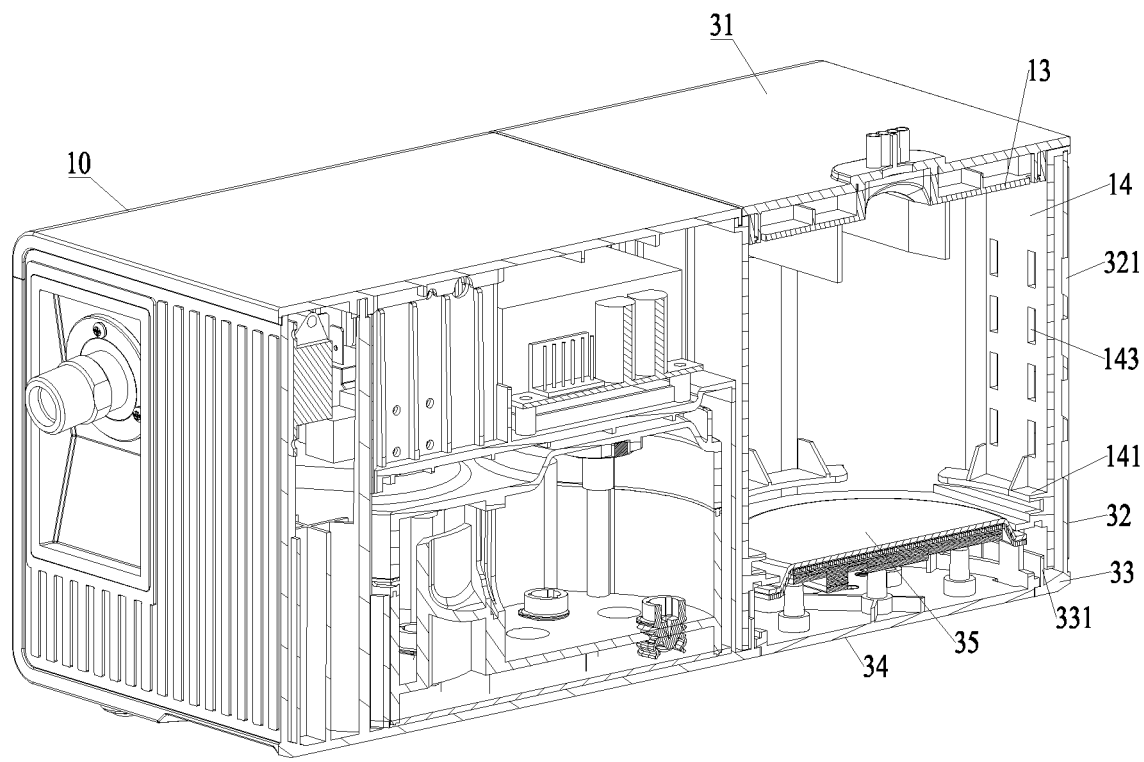
FIG. 3 is a vertically sectioned perspective view of an embodiment of the ventilation treatment apparatus in the present invention.

To solve the above problems, the present invention provides a water tank mounting structure for a ventilation treatment apparatus, comprising a cavity 11 for containing a water tank 20 and a side wall for defining the cavity 11, wherein the side wall comprises an inner side wall 14 and an outer side wall 32 spaced apart from each other, a first gas hole 143 is provided in the inner side wall 14, a second gas hole 321 is provided in the outer side wall 32, and the first gas hole 143 and the second gas hole 321 are arranged in a staggered manner in a direction perpendicular to the side wall (see the left-right direction in FIG. 3).

Compared with the prior art, in the water tank mounting structure in the present invention, the side wall for defining the cavity 11 is configured into a two-layer structure (i.e., including an inner side wall 14 and an outer side wall 32), and a first gas hole 143 and a second gas hole 321 are arranged in the inner side wall 14 and the outer side wall 32 respectively, so that the hot gas in the cavity 11 can be effectively vented through the first gas hole 143 and the second gas hole 321; besides, by arranging the first gas hole 143 and the second gas hole 321 in a staggered manner, when external water enters through the second gas hole 321, the water flows downwards along the side wall without invading into the cavity 11, thus a waterproof effect is achieved.

It should be noted: in the present invention, the side wall mentioned above should be the side wall located outside, such as the right side wall of the ventilation treatment apparatus shown in FIG. 3. Of course, in other types of ventilation treatment apparatuses, the side wall may be another side wall adjacent to the external environment.

Figure 4:
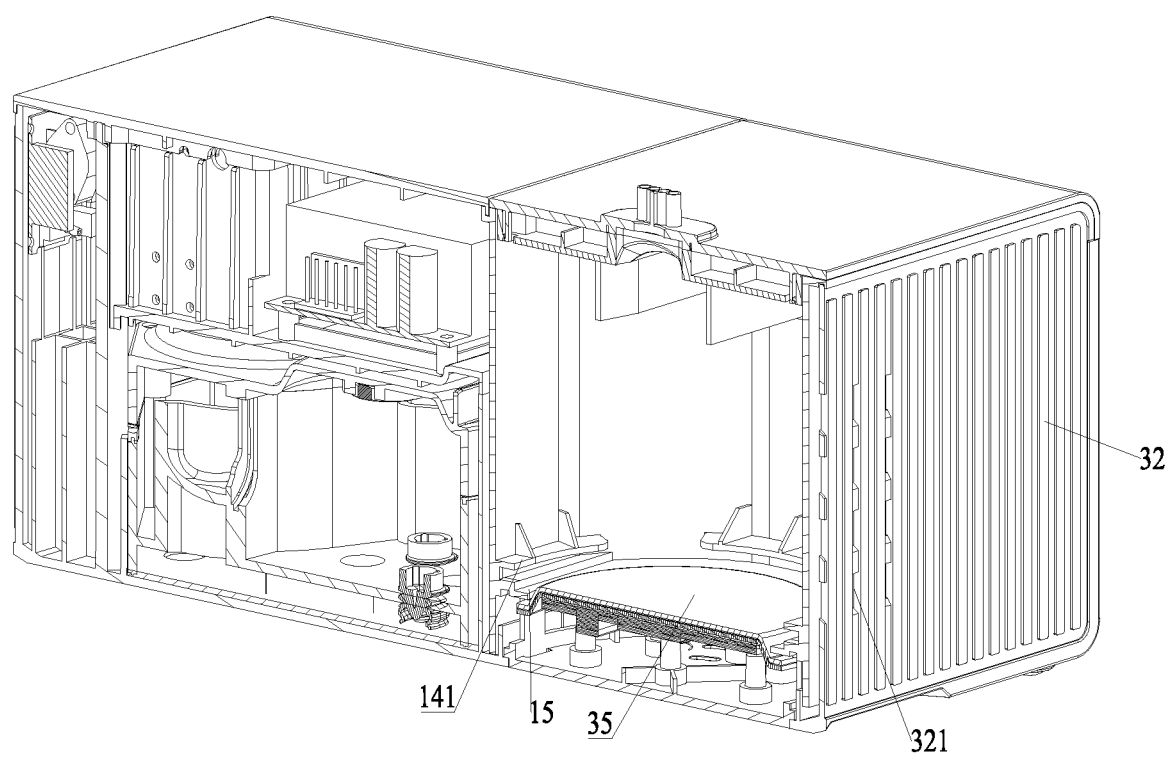
FIG. 4 is a schematic diagram of the ventilation treatment apparatus in FIG. 3 from another viewing angle.

In order to enhance the gas permeability of the cavity 11, the inner side wall 14 may be provided with a plurality of first gas holes 143, and the outer side wall 32 may be provided with a plurality of second gas holes 321. The plurality of first gas holes 143 and the plurality of second gas holes 321 may be arranged in any way. For example, as shown in FIGS. 3 and 4, the plurality of first gas holes 143 may be spaced apart from each other in the height direction of the inner side wall 14 and arranged in rows in the width direction of the inner side wall 14, and the plurality of second gas holes 321 may be spaced from each other in the height direction of the outer side wall 32 and arranged in rows in the width direction of the outer side wall 32. In addition, the first gas holes 143 and the second gas holes 321 may be in the same shape or different shapes, such as circular shape, square shape, or triangular shape, etc.

In the present invention, the cavity 11 may be in different shapes, depending on the shape and structure of the ventilation treatment apparatus and the shape of the water tank 20; furthermore, the side wall for defining the cavity 11 may be arranged in different ways. The inner side wall 14 and the outer side wall 32 may have the same extension direction or different extension directions, as long as there is spacing between them. According to an embodiment of the present invention, as shown in FIG. 3, the inner side wall 14 is parallel to the outer side wall 32, and both the inner side wall 14 and the outer side wall 32 extend in the vertical direction.

During use, when external water enters into the spacing between the inner side wall 14 and the outer side wall 32 from the second gas hole 321, the water can't directly enter into the cavity 11 through the first gas hole 143 because the first gas hole 143 and the second gas hole 321 are staggered from each other; instead, the water will flow downward to the bottom of the side wall under the blocking action of the inner side wall 14 opposite to the second gas hole 321. Furthermore, to drain off the water flowing to the bottom of the side wall timely, the water tank mounting structure in the present invention may further comprise a guide channel arranged on the bottom of the side wall for guiding out the water between the outer side wall 32 and the inner side wall 14.

There is no particular restriction on the specific structure of the guide channel in the present invention. According to an embodiment of the present invention, as shown in FIG. 3, the water tank mounting structure comprises a bottom plate 33 extending inward from the bottom of the outer side wall 32 and a stop rib 331 that extends upward from the bottom plate 33 and spaced from the outer side wall 32, the stop rib 331 is located on the inner side of the inner side wall 14, the guide channel is defined by the outer side wall 32, the bottom plate 33, and the stop rib 331, and the bottom plate 33 is provided with a drain port. According to another embodiment of the present invention, the water tank mounting structure comprises a bottom plate 33 connected between the outer side wall 32 and the inner side wall 14, the guide channel is defined by the outer side wall 32, the inner side wall 14 and the bottom plate 33, and the bottom plate 33 is provided with a drain port.

It should be noted: when the water flows into the guide channel, the bottom plate 33 and the drain port shall cooperate with each other to guide the water to the drain port so that the water is drained. For example, the bottom plate 33 may be disposed obliquely (see FIG. 3), and the drain port may be disposed at the lower end of the bottom plate 33.

Figure 2:
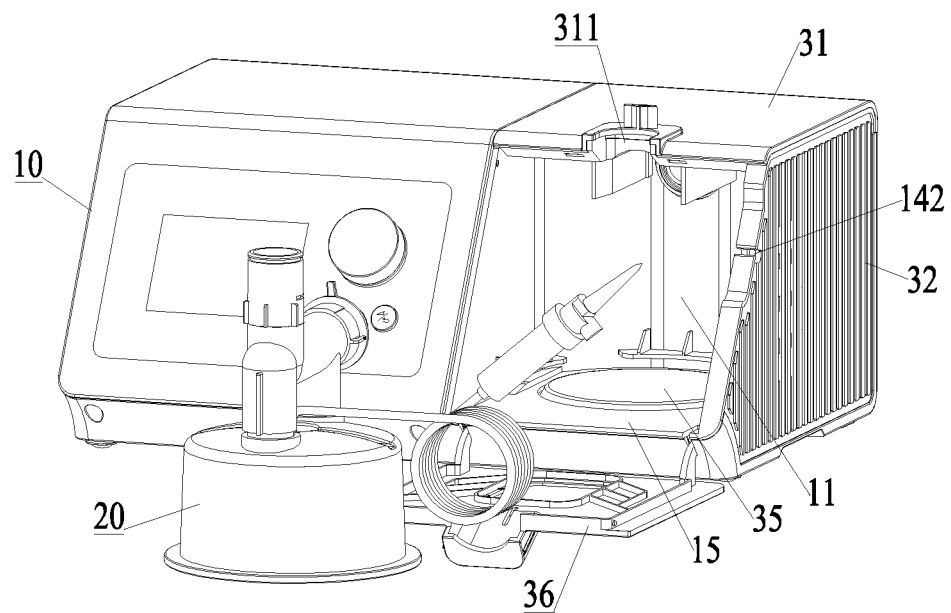
FIG. 2 is a schematic diagram of the water tank in FIG. 1 before the water tank is mounted on the main unit.
Figure 15:
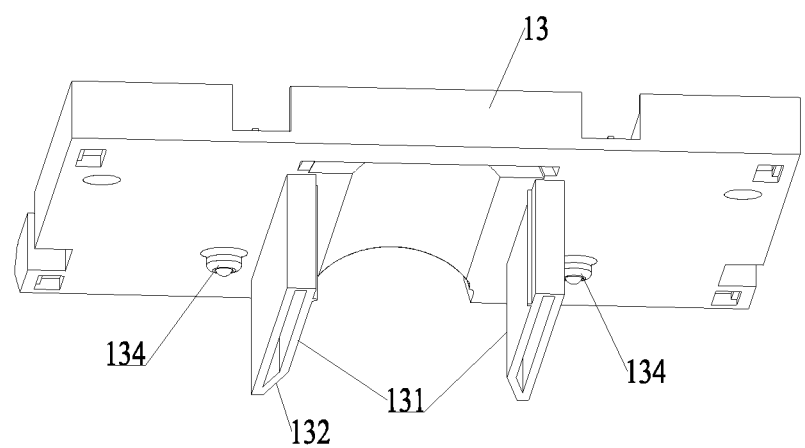
FIG. 15 is a schematic diagram of the inner top wall and guiding plate in FIG. 14 from another viewing angle.
Figure 16:
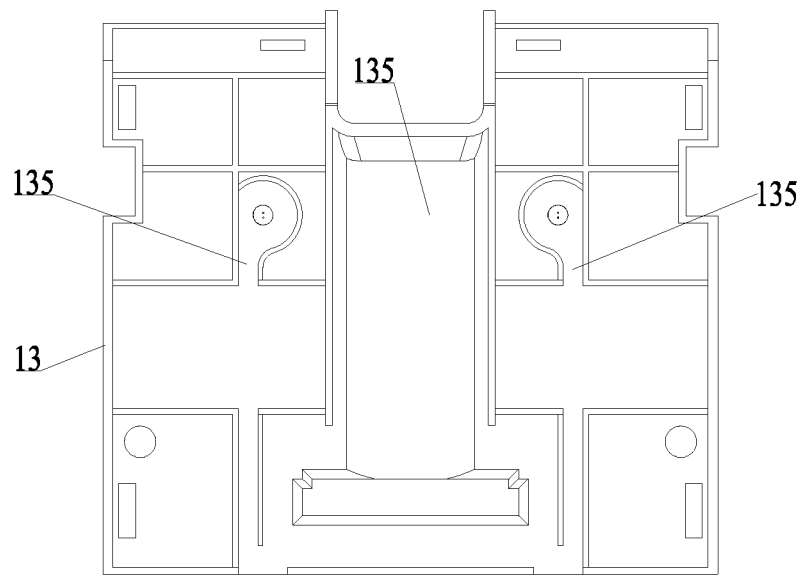
FIG. 16 is a top view of the inner top wall in FIG. 15.

In addition, in the present invention, the water tank mounting structure further includes a top wall for defining the cavity 11, the top wall preferably comprises an inner top wall 13 and an outer top wall 31 that are spaced apart from each other (see FIGS. 3 and 4), which is to say, the top wall is also configured into a double-layer structure, thus the strength of the water tank mounting structure can be improved, and other functional components may be arranged on the top wall so as to improve the use of the ventilation treatment apparatus and optimize the structure of the ventilation treatment apparatus. Specifically, for example, as shown in FIGS. 1 and 2, since the top wall of the cavity 11 is in a normally covered state, the interior of the cavity 11 is dark. Therefore, an illuminating component for illuminating the cavity 11, such as a LED lamp 134 (see FIGS. 14 and 15), may be provided on the inner top wall 13. Moreover, for example, as shown in FIG. 16, a wiring groove 135 may also be provided in the upper surface of the inner top wall 13 for internal wiring in the ventilation treatment apparatus. The wiring groove 135 may be defined by ribs protruding upward from the top surface of the inner top wall 13, and may be formed together with the outer top wall 31.

Moreover, as shown in FIGS. 1-5, the water tank mounting structure may further comprise a bottom wall 15 for defining the cavity 11, a base 34 located below the bottom wall 15 and a heating plate 35, wherein the bottom wall 15 is provided with an opening for containing the heating plate 35, and the base 34 is provided with a supporting component for supporting the heating plate 35 at the opening. When the water tank 20 is mounted in the cavity 11, the heating plate 35 may contact with the bottom of the water tank 20, so as to heat up the water in the water tank 20.

Figure 5:
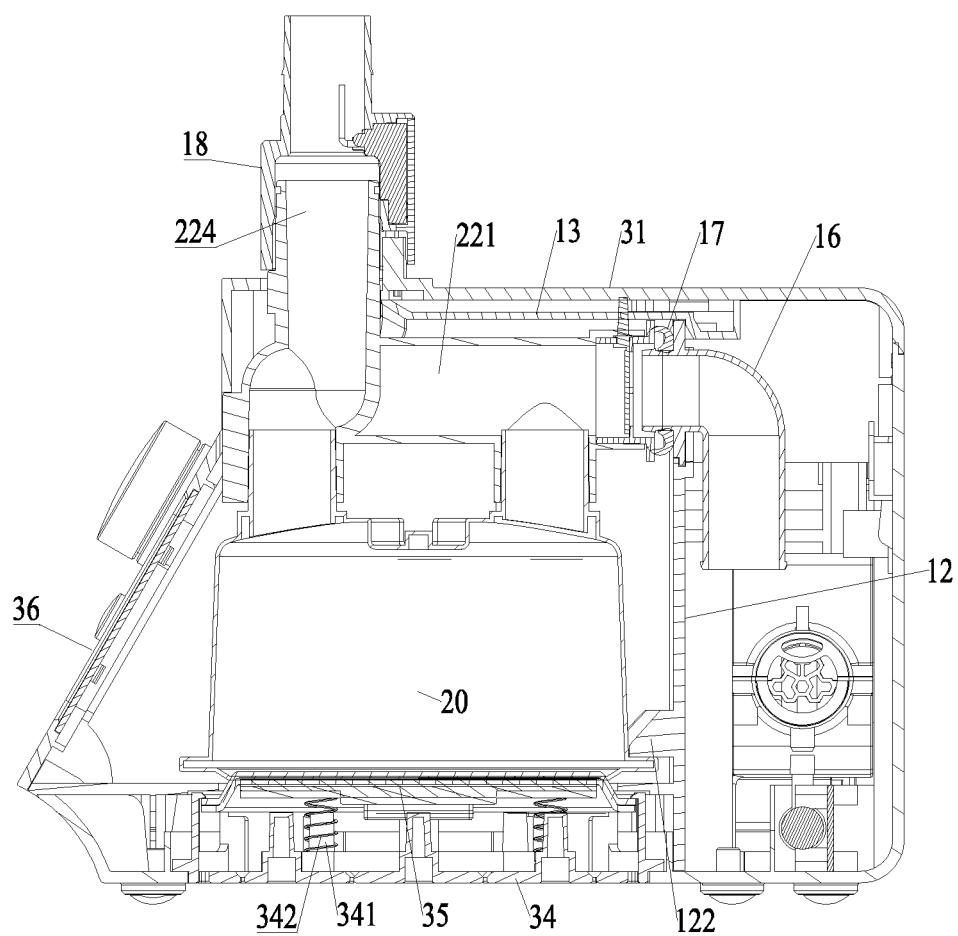
FIG. 5 is a vertical sectional view of an embodiment of the ventilation treatment apparatus in the present invention.

As shown in FIG. 5, the supporting component may comprise a supporting column 341 extending upward from the top surface of the base 34, and a spring 341 sleeved on the supporting column 342 with a top end abutting against the bottom surface of the heating plate 35. The spring 342 can force the heating plate 35 to adhere to the bottom of the water tank 20, so as to improve the heating efficiency and attain a shockproof effect. The heating plate 35 may be shaped and sized to match the bottom of the water tank 20. The base 34 is preferably detachable, in order to facilitate the maintenance and replacement of the components.

Figure 7:
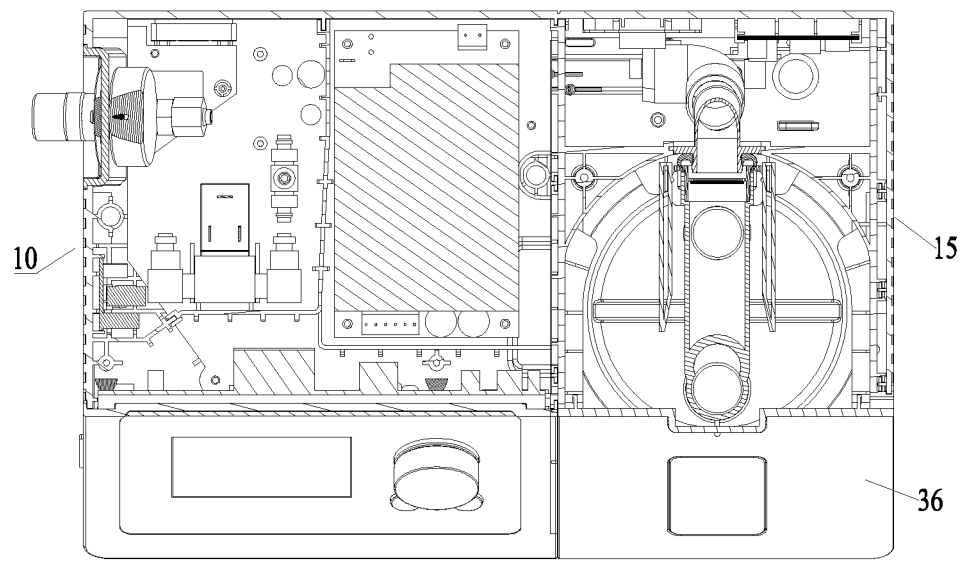
FIG. 7 is a cross sectional view of an embodiment of the ventilation treatment apparatus in the present invention.
Figure 8:
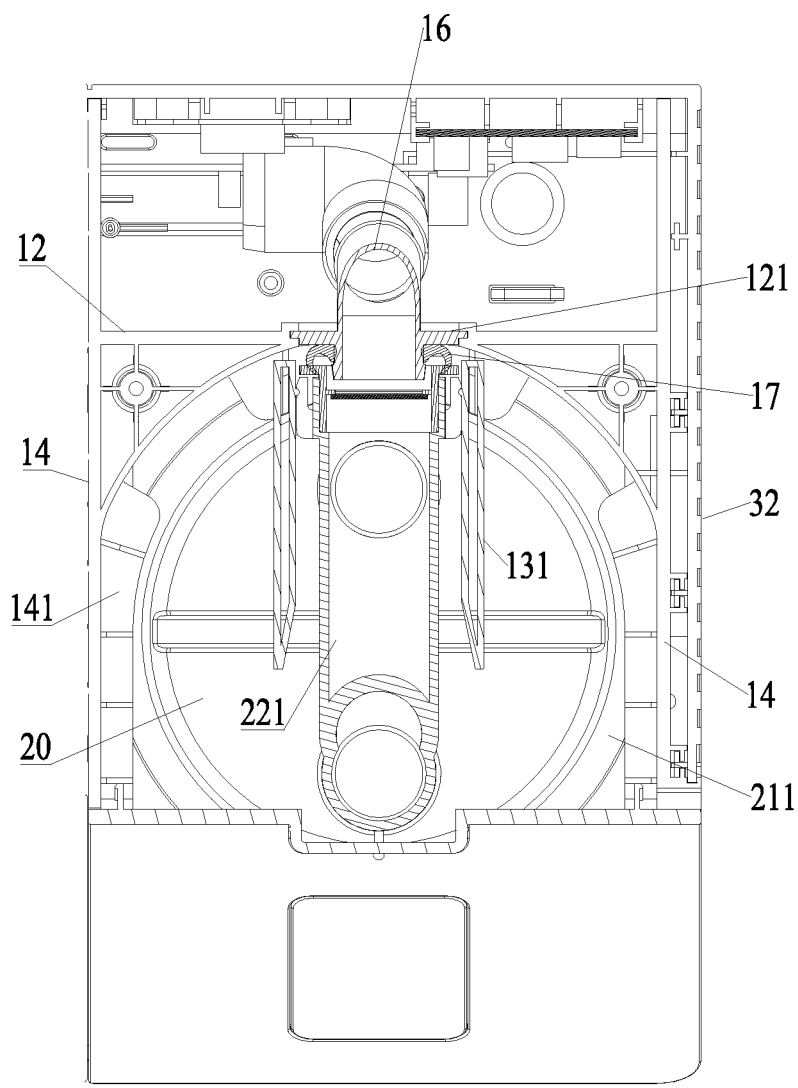
FIG. 8 is a schematic partial view of the structure in FIG. 7.

There is no guiding structure for guiding the assembling of the water tank in existing humidifying devices. Consequently, the assembling efficiency of the water tank is low, and the intake tube for ventilation to the water tank of the ventilation treatment apparatus may be misaligned to the gas inlet of the water tank easily, resulting in gas leakage. To solve the above problems, according to an embodiment of the present invention, as shown in FIGS. 7 and 8, the water tank mounting structure may further comprise a back wall 12 for defining the cavity 11, with an opening 121 for mounting the intake tube 16 of the ventilation treatment apparatus arranged in the back wall 12; the water tank mounting structure may further comprise a guiding assembly for guiding the water tank 20 to assemble to the cavity 11 in a way that the gas inlet 222 of the water tank 20 is aligned to the opening 121.

It can be understood that usually the respiratory gas should be charged into the water tank 20 through the gas inlet 222 of the water tank 20 via the intake tube 16, and the respiratory gas is humidified in the water tank 20 and then delivered to the user during the use of the ventilation treatment apparatus. In the present invention, by providing the guiding assembly, the gas inlet 222 of the water tank 20 can be aligned to the opening 121 where the intake tube 16 is mounted while the water tank 20 is guided to assemble to the cavity 11, so as to facilitate the mounting of the water tank 20 of the water tank mounting structure and prevent gas leakage resulted from the misalignment of the gas inlet 222 from the opening 121.

It should be noted that the cavity 11 may be shaped to match the shape of the water tank 20, and the cavity 11 has an opening for mounting and removing the water tank 20.

To make the technical scheme of the present invention understood more clearly, the present invention provides a specific water tank structure. Here the guiding assembly will be described in detail with reference to the specific water tank structure. It should be understood that the specific structures of the water tank and the guiding assembly in the present invention are not limited to the structures described here.

Figure 9:
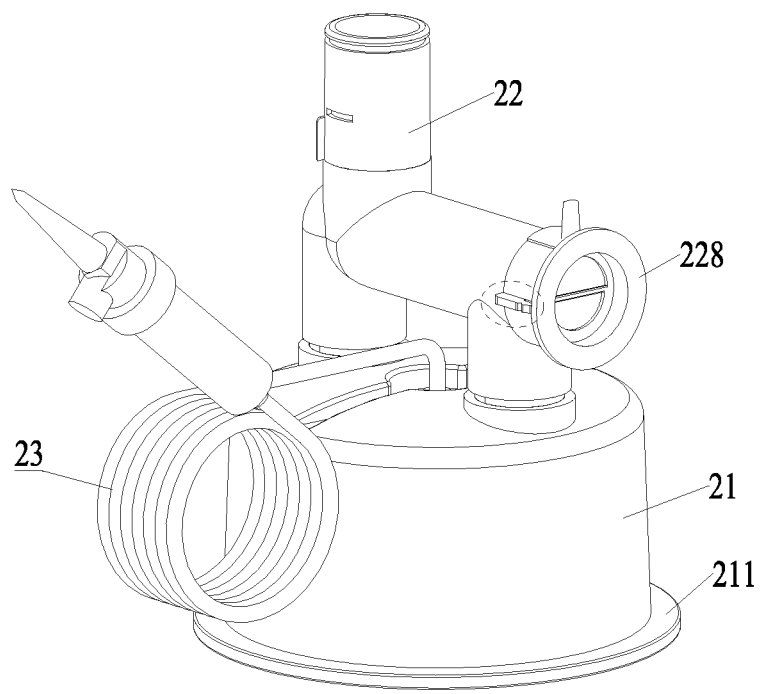
FIG. 9 is a perspective view of an embodiment of the water tank in the present invention.
Figure 12:
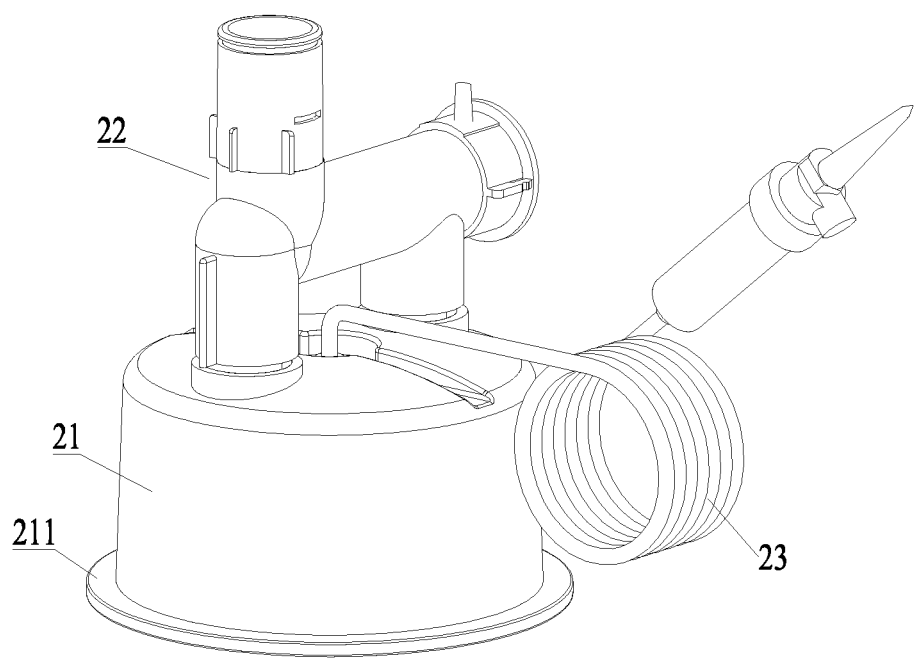
FIG. 12 is a perspective view of the water tank in FIG. 9 from another viewing angle.
Figure 13:
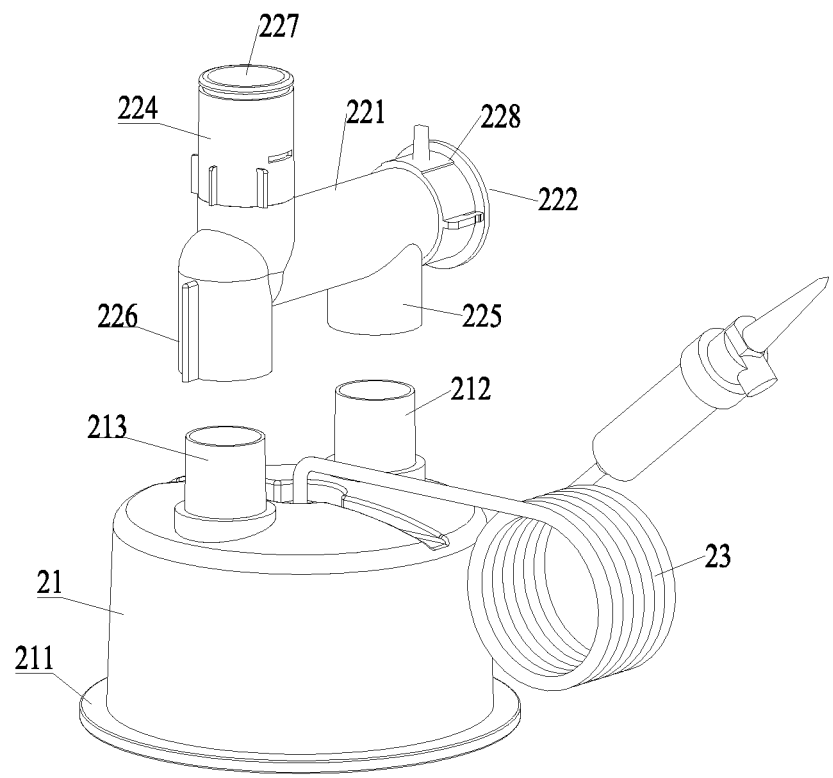
FIG. 13 is an exploded view of the structure in FIG. 12.

For example, as shown in FIGS. 9, 12 and 13, the water tank 20 comprises a main body 21 and an adapter 22 connected above the main body 21. A water storage cavity is defined in the main body 21, the main body 21 is provided with a first interface 212 for venting to the water storage cavity and second interface 213 for leading out the gas humidified in the water storage cavity and delivering the gas to the user. The adapter 22 comprises a horizontal tube 221 extending in the horizontal assembling direction of the water tank 20 and a vertical tube 224 communicating with the horizontal tube 221 and extending in the vertical direction, the horizontal tube 221 is provided with a third interface 225 and a fourth interface 226 for connecting with the first interface 212 and the second interface respectively, and an end of the horizontal tube 221 oriented to the back wall 12 is the gas inlet 222. It can be understood: after the water tank 20 is assembled to the cavity 11, the end of the horizontal tube 221 oriented to the back wall 12 is connected with the intake tube 16; during the use, the gas in the intake tube 16 enters into the horizontal tube 221 through the gas inlet 222, then enters into the main body 21 via the third interface 225 and the first interface 212, the gas is humidified in the main body 21, then enters into the vertical tube 224 via the second interface 213 and the fourth interface 226, and then is discharged through the gas outlet 227 at the end of the vertical tube 224 away from the horizontal tube 221.

In addition, as shown in FIGS. 9, 12 and 13, the main body 21 may be further connected with a water injection tube 23 for injecting water into the water storage cavity. The water tank 20 shown in the drawings of the present invention is a water tank that has an automatic water replenishment function and can maintain maximum evaporation and constant low water level in it. Thus, it can not only meet the requirement for humidifying high-flow gas but also provide enough space to mix the respiratory gas with water vapor more uniformly.

Of course, in order to further ensure the airtightness between the intake tube 16 and the horizontal tube 221, a sealing element 17 may be provided at the joint between the intake tube 16 and the horizontal tube 221. In the case that the connection between the intake tube 16 and the horizontal tube 221 is made by inserting the intake tube 16 into the horizontal tube 221, the sealing element 17 may be a seal ring sleeved on the intake tube 16, as shown in FIG. 8.

Based on the above water tank structure, the guiding assembly may comprise a first guiding component to be fitted with the horizontal tube 221 to guide the assembling of the water tank 20 and/or a second guiding component to be fitted with the main body 21 to guide the assembling of the water tank 20. Preferably, the guiding assembly comprises a first guiding component and a second guiding component, so that the top part and the bottom part of the water tank 20 are fitted with the first guiding component and the second guiding component respectively to guide the assembling of the water tank 20; thus, the smoothness of movement of the water tank 20 can be improved, and the guiding effect on the water tank 20 can be improved as well, so that the assembling of the water tank 20 is more reliable.

According to an embodiment of the present invention, as shown in FIGS. 1-4 and 14-15, the first guiding component comprises two guiding plates 131 protruding downward from the inner top wall 13 and extending in the assembling direction, the two guiding plates 131 are spaced from each other at the two sides of the opening 121 in a direction perpendicular to the assembling direction, and the horizontal tube 221 can enter into the spacing between the two guiding plates 131. During the assembling of the water tank 20, after the water tank 20 is led into the cavity 11 through the opening of the cavity 11, the horizontal tube 221 will be inserted between the two guiding plates 131 as the water tank 20 is moved, so that the gas inlet 222 at one end of the horizontal tube 221 is aligned to the opening 121 and the water tank 20 is assembled in the correct position.

Figure 14:
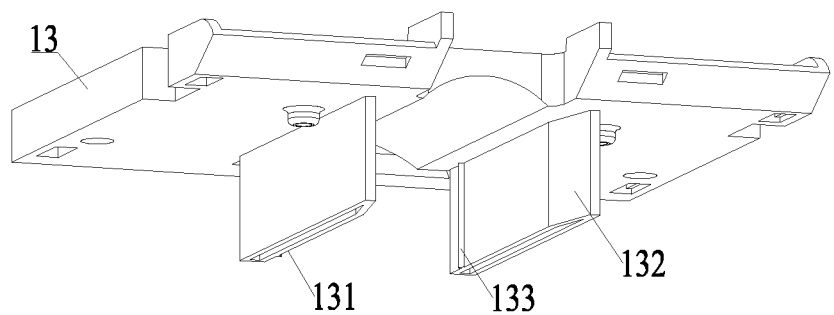
FIG. 14 is a schematic structural diagram of the inner top wall and guiding plate in the present invention.

To facilitate the horizontal tube 221 to enter into the spacing between the two guiding plates 131 smoothly during the assembling, a guiding bevel 132 may be formed on the end of each guiding plate 131 away from the opening 121, as shown in FIGS. 8 and 14.

In another embodiment of the water tank mounting structure in the present invention, the water tank mounting structure may further comprise a positioning structure for positioning the water tank 20 in its assembling position. It can be understood that the assembling position refers to the position where the water tank 20 is mounted correctly in the cavity 11. By arranging the positioning structure, the reliability of mounting of the water tank 20 can be improved, and gas leakage caused by the swaying of the water tank 20 in the cavity 11 or the loosening of other connecting components can be avoided.

The positioning structure may be implemented in different ways, and there is no particular restriction on the specific implementation of the positioning structure in the present invention. For example, the positioning structure may be positioning posts and positioning holes that are arranged on the cavity 11 and the water tank 20 and fitted with each other. To make the water tank mounting structure simpler, reduce the manufacturing cost and ensure effective positioning of the water tank 20, according to a preferred embodiment of the present invention, the positioning structure comprises a flange 133 provided on one of the inner side of the guiding plate 131 and the outer wall of the horizontal tube 221, and a groove 223 provided on the other of the inner side of the guiding plate 131 and the outer wall of the horizontal tube 221 to be fitted with the flange 133. During the assembling, when a click sound is heard as the horizontal tube 221 is moved along the guiding plate 131, it indicates that the flange 133 is embedded in the groove 223 and the water tank 20 is mounted in the correct position. Thus, it is seen that the position of the flange 133 must correspond to the position of the groove 223 so that the flange 133 is embedded in the groove 223 when the water tank 20 reaches its assembling position.

Figure 10:
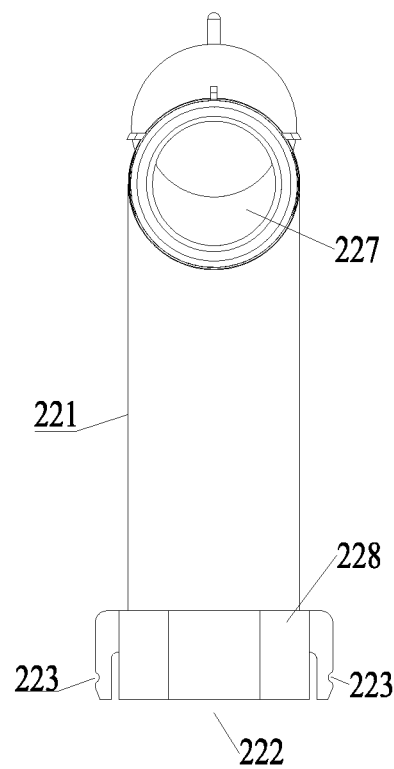
FIG. 10 is a top view of the adapter in FIG. 9.
Figure 11:
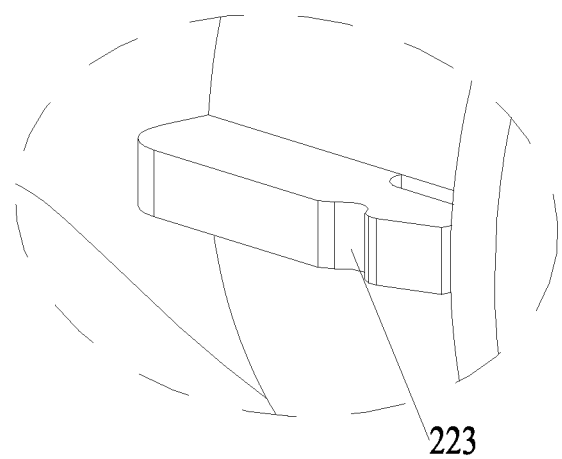
FIG. 11 is a partially enlarged view of the structure in FIG. 9.

Furthermore, as shown in FIGS. 9, 12 and 13, in order to prevent the gas entering the horizontal tube 221 from flowing backward into the intake tube 16, a check valve 228 may be provided at the gas inlet 222 of the horizontal tube 221, so that the gas can only flow into the horizontal tube 221 from the intake tube 16. In that case, a groove 223 may be arranged in the outer wall of the check valve 228 (see FIGS. 10 and 11), and a flange 133 may be arranged on the inner side of guiding plate 131 at the end near the opening 121 (see FIG. 14).

Figure 6:
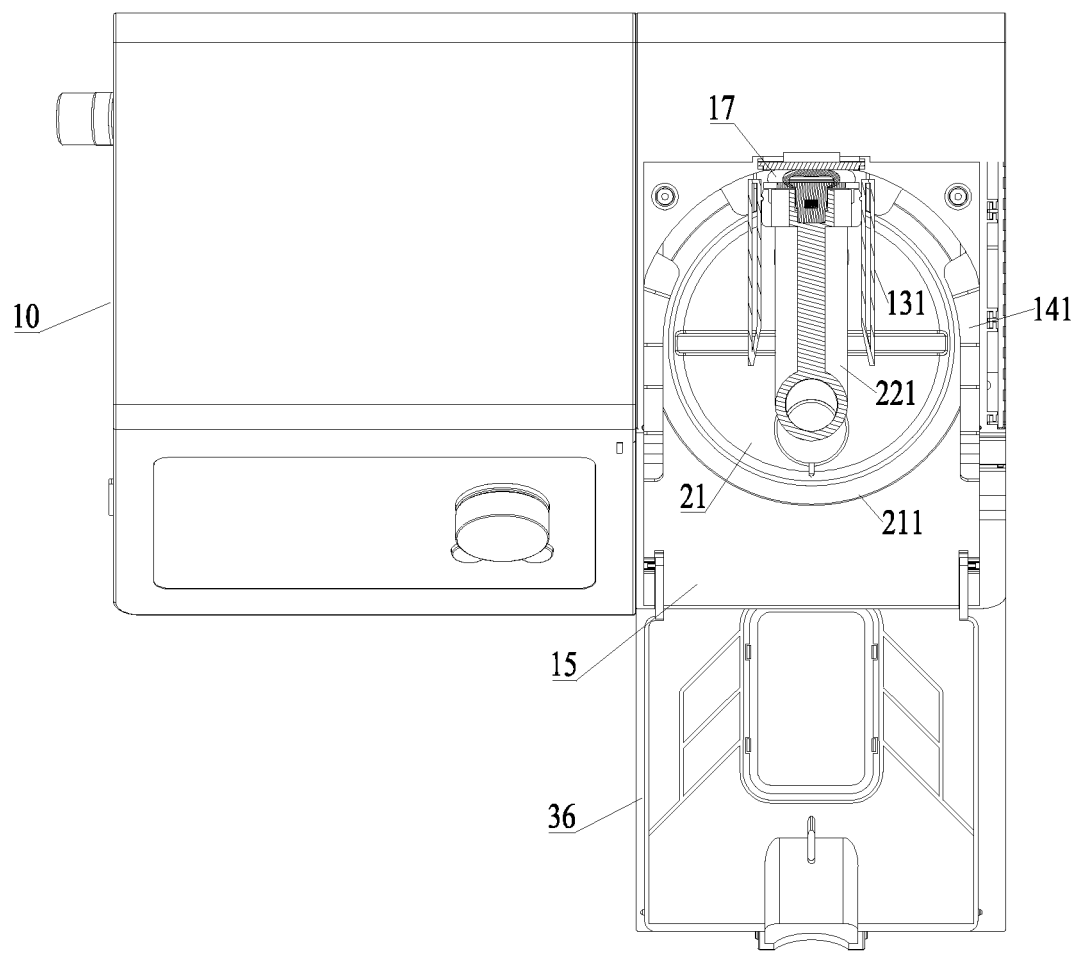
FIG. 6 is a top view of the ventilation treatment apparatus in FIG. 1, in which a partial sectional view is included to illustrate the water tank mounting structure.

In the present invention, for the second guiding component, according to an embodiment of the present invention, the water tank mounting structure comprises two side walls arranged opposite to each other for defining the cavity 11, the second guiding component may comprise two guide rails 141 arranged on the two side walls respectively (see FIGS. 6-8), and a sliding part that can be fitted with the two guide rails 141 and slide along the guide rails 141 may be provided on the main body 21.

Furthermore, the cross section of the main body 21 may be circular, the sliding part may be an annular convex edge 211 protruding outward from the outer circumferential surface of the main body 21 and extending in the circumferential direction of the main body 21, the guide rails 141 comprise two guiding ribs that protrude from the inner surface of the side wall and extend in the assembling direction, and are spaced apart from each other in the height direction of the side wall, and the annular convex edge 211 can enter into the spacing between the two guiding ribs (see FIGS. 3 and 4).

During the assembling of the water tank 20, the horizontal tube 221 enters into the spacing between the two guiding plates 131 and the two sides of the annular convex edge 211 enter into the two guide rails 141 respectively as the water tank 20 enters into the cavity 11 through the opening of the cavity 11; under the guidance of the guiding plates 131 and the guide rails 141, the gas inlet 222 of the water tank 20 is aligned and gradually approaches to the opening 121; when a click sound is heard, it indicates that the flange 133 is embedded in the groove 223 and the water tank 20 reaches its assembling position and is fixed in the assembling position.

Preferably, the spacing between the two guide rails 141 is decreased in the assembling direction to prevent the main body 21 to move further in the assembling direction after it reaches the assembling position. The decreasing may be gradual decreasing, or may be in the form as shown in FIG. 8, for example. In addition, as shown in FIG. 5, a limiting rib 122 may be provided on the back wall 12, and has spacing from the bottom wall 15 (described below) in the vertical direction; when the water tank 20 reaches the assembling position, the back side of the annular convex edge 211 may be inserted into the spacing, and thereby the water tank 20 is fixed.

The water tank mounting structure in the present invention is applicable to any type of ventilation treatment apparatus. For example, the water tank mounting structure may be applied in a ventilation treatment apparatus in which the main unit and the humidifying device are separate components; in such a ventilation treatment apparatus, the water tank mounting structure is arranged on the humidifying device; alternatively, the water tank mounting structure may be applied in a ventilation treatment apparatus in which the main unit and the humidifying device are formed integrally, such as the ventilation treatment apparatus shown in FIGS. 1-8 in the present invention, which comprises a main unit 10, a water tank 20, and the water tank mounting structure described above, wherein the water tank mounting structure is arranged on the main unit 10. In such a ventilation treatment apparatus, the humidifying device is arranged on the main unit 10 and becomes a part of the main unit 10; thus, the structure of the ventilation treatment apparatus is more compact, and the ventilation treatment apparatus is portable.

Specifically, as shown in FIG. 3, the main unit 10 comprises a casing 30, which comprises a double-layer top wall (i.e., an outer top wall 31 and an inner top wall 13), double-layer side walls (i.e., outer side walls 32 and inner side walls 14), a bottom plate 33 and a base 34. The base 34 is detachably mounted to the bottom plate 33 by means of a snap-fit structure (see FIG. 3). Of course, in other embodiments, the base 34 and the bottom plate 33 may be formed integrally.

As shown in FIGS. 1 and 2, the casing 30 is provided with an opening for inserting/removing the water tank 20, and the main unit 10 may further comprise a front cover 36 that can cover the opening of the casing 30, and the bottom end of the front cover 36 may be hinged to the casing 30 to open the front cover 36 by turning the front cover 36 downward, so that the water tank 20 can be pushed into the casing 30. The downward turning scheme for opening the cover is convenient and labor-saving, and ensures integral appearance and application safety of the ventilation treatment apparatus.

As shown in FIGS. 1 and 2, owing to the existence of the adapter 22 in the water tank 20, a notch 311 for making room for the adapter 22 may be formed in the double-layer top wall, in order to prevent the water tank 20 from occupying a large space of the main unit 10 and reduce the size of the main unit 10. When the water tank 20 is assembled in position, the vertical tube 224 of the adapter 22 is embedded in the notch 311, and the existence of the notch 311 achieves a fixing and positioning effect on the water tank. In addition, the gas outlet 227 of the adapter 22 may be directly connected with the respiratory mask through a gas tube; alternatively, as shown in FIG. 5, the top end of the adapter 22 may be connected with a heating tube connector 18, so that the humidified gas can be conveyed to a heating tube, heated in the heating tube, and then conveyed to the respiratory mask.

Moreover, to facilitate water injection from an external water source into the water tank 20 at any time, as shown in FIG. 2, the casing 30 may be provided with a mounting slot 142 for mounting a water injection tube 23 of the water tank 20 therein. It can be understood that the mounting slot 142 penetrates the double-layer side wall, so that the water injection tube 23 extends out of the casing 30.

At present, many ventilation treatment apparatus available on the market, such as oxygen therapeutic instruments or high-flow oxygen therapeutic instruments, have no separate oxygen isolation space. Once leakage occurs at the seal of the tube for oxygen supply, the oxygen will diffuse into the entire main unit without any obstruction. Since electronic components (e.g., circuit boards) are usually arranged in the main unit, the risk that the electronic components become ignition sources will be increased in folds and even a fire disaster may occur in the oxygen-enriched environment. In order to solve the above problems, the present invention provides a ventilation treatment apparatus, which may comprise a casing 410 and an oxygen assembly 420, wherein a main unit cavity is defined in the casing 410, and a partition assembly is arranged in the main unit cavity and separates an airtight oxygen isolation chamber 413 in the main unit cavity, and the oxygen assembly 420 is mounted in the oxygen isolation chamber 413.

In the present invention, by arranging a partition assembly in the main unit cavity to separate an oxygen isolation chamber 413 and mounting the oxygen assembly 420 (i.e., components related with oxygen, such as oxygen supply tube, and oxygen proportioning valve for regulating the oxygen flow, etc.) in the oxygen isolation chamber 413, the oxygen assembly 420 is isolated from the electronic components in the main unit, such as circuit boards, etc. Thus, once the oxygen leaks, it will not diffuse into other areas of the main unit cavity immediately; instead, the oxygen will be enclosed in the separate oxygen isolation chamber 413, thereby the reliability and safety of the ventilation treatment apparatus are improved.

It is well-known that the main unit cavity of an existing ventilation treatment apparatus (e.g., respirator) usually is further provided with a fan for providing respiratory gas and a power supply adapter for supplying power, etc. In order to simplify the main unit cavity structure and reduce the manufacturing cost of the ventilation treatment apparatus while separating the oxygen isolation chamber 413 in the main unit cavity, the partition assembly may be arranged in the main unit cavity in a way that a fan chamber 414 and a power supply chamber 415 are separated in the main unit cavity. That is to say, the partition assembly can divide the main unit cavity into an oxygen isolation chamber 413, a fan chamber 414 and a power supply chamber 415, thus the arrangement of the components in the main unit cavity is neat and modular, and thereby the layout rationality and space utilization of the main unit cavity are improved.

Figure 17:
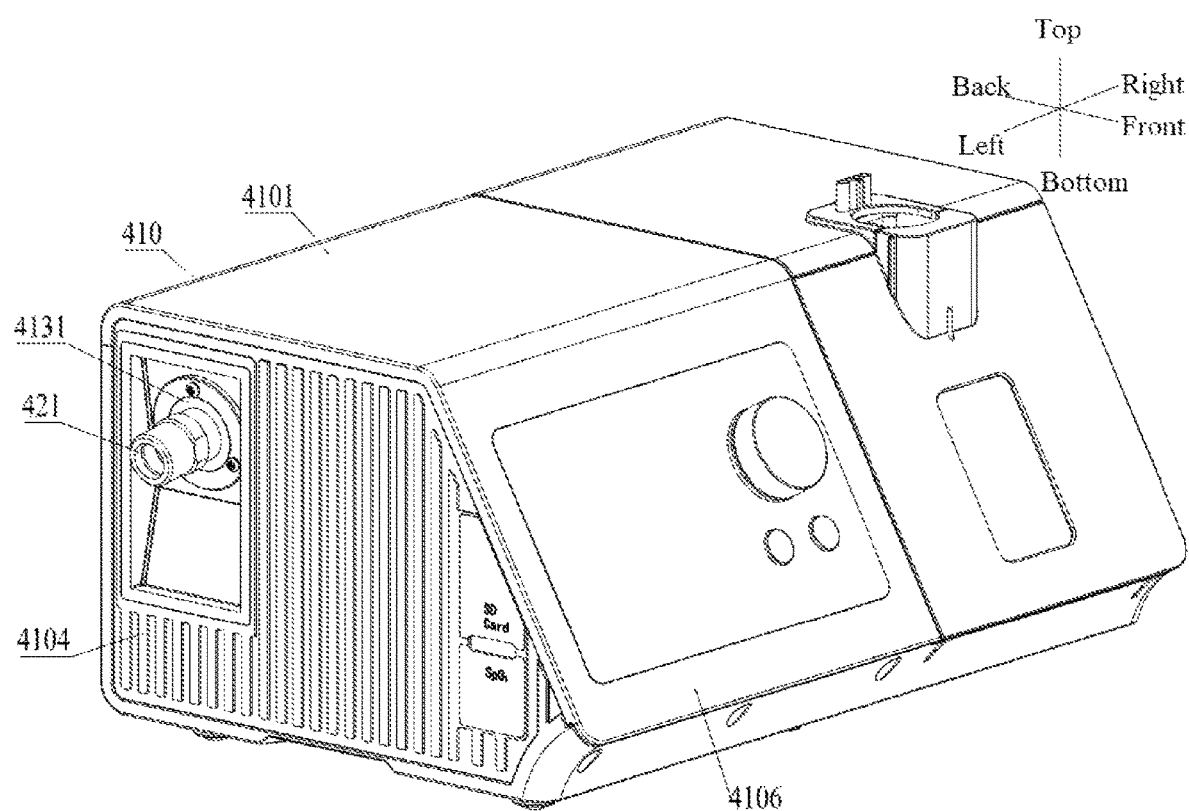
FIG. 17 is a perspective view of another embodiment of the ventilation treatment apparatus in the present invention.
Figure 18:
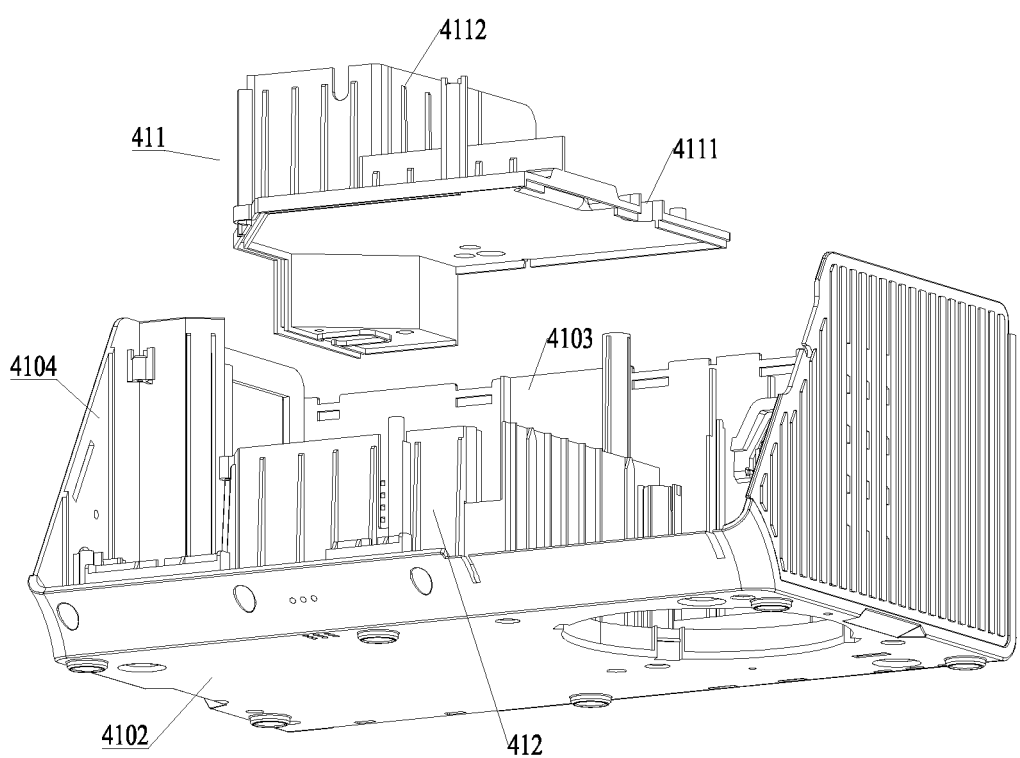
FIG. 18 is a structural schematic diagram of the partition assembly and lower housing in the present invention.
Figure 19:
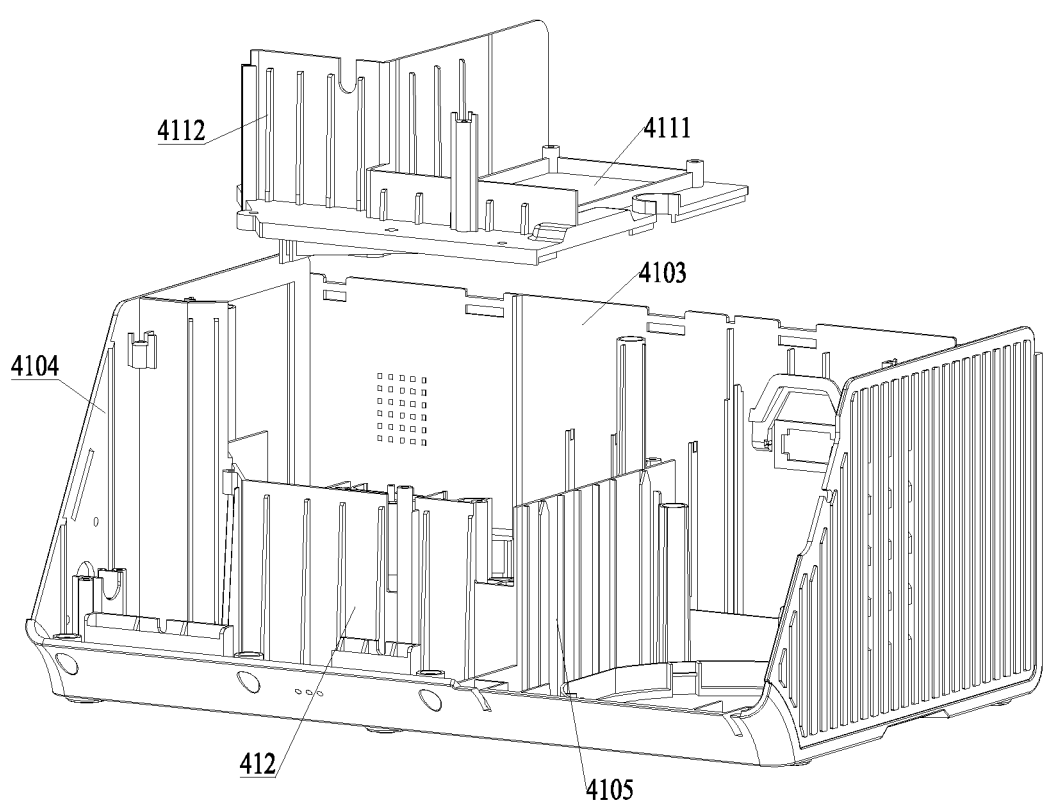
FIG. 19 is a schematic diagram of the structure in FIG. 18 from another viewing angle.

Specifically, according to an embodiment of the present invention, as shown in FIGS. 17-19, the casing 410 comprises a top wall 4101 and a bottom wall 4102 for defining the main unit cavity, and the partition assembly comprises an upper partition 411, which comprises bottom plates 4111 that are arranged in a spaced manner above the bottom wall 4102 and divide the main unit cavity into an upper cavity and a lower cavity, the oxygen isolation chamber 413 is located in the upper cavity, and the fan chamber 414 is located in the lower cavity. In view that the fan chamber 414 is used for mounting the fan assembly that is heavy, the center of gravity of the entire apparatus can be lowered by arranging the fan chamber 414 in the lower cavity, and thus the stability of arrangement of the apparatus is improved.

Furthermore, as shown in FIGS. 18 and 19, a power supply chamber 415 is arranged in the main unit cavity, the partition assembly further comprises an upper side plate 4112 that extends from the bottom plates 4111 upward to the top wall 4101 and separates the upper cavity into a left cavity and a right cavity, and the oxygen isolation chamber 413 and the power supply chamber 415 are located in either of the left cavity and the right cavity respectively.

Figure 21:
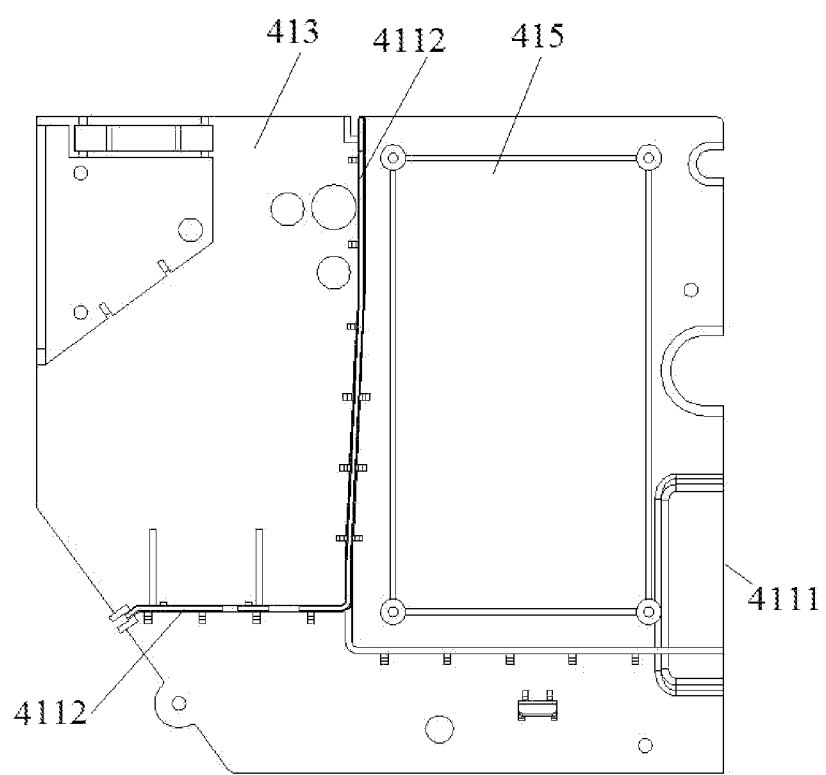
FIG. 21 is a top view of the upper partition in FIG. 19.

Furthermore, as shown in FIGS. 18, 19 and 21, the casing 410 comprises a back wall 4103, a left side wall 4104 and a right side wall 4105 for defining the main unit cavity, the oxygen isolation chamber 413 is defined by the top wall 4101, the bottom plate 4111, the left side wall 4104 and the upper side plate 4112, and the power supply chamber 415 is defined by the top wall 4101, the bottom plate 4111, the right side wall 4105 and the upper side plate 4112. A ventilation treatment apparatus, such as respirator, usually is equipped with a humidifying device to increase the humidity of the inhaled gas. By warming and humidifying the gas flow through the humidifying device, the adverse effects caused by mycterxerosis (e.g., nasal obstruction and nasal bleeding, etc.) can be reduced, and the resistance in the nasal cavity can be decreased, the stability of the pressure in the respiratory mask can be ensured effectively, thereby the treatment effect and adaptability of the respirator can be improved. In order to make the structure of the respirator more compact, smaller and portable, the humidifying device and the main unit are formed integrally, for example, as shown in FIG. 17, the humidifying device is located on the right side of the main unit. That is to say, the casing 410 of the ventilation treatment apparatus may comprise a main unit cavity and a humidifying cavity 418 (i.e., a cavity for mounting the humidifying device). In the present invention, with the above arrangement, the power supply chamber 415 is arranged close to the humidifying cavity 418 located on the right side, and the oxygen isolation chamber 413 is arranged close to the outside, so that the power supply chamber 415 can supply power to the humidifying device and oxygen can be supplied to the oxygen isolation chamber 413 conveniently. For example, an external power supply interface (may be connected with 220V voltage) may be arranged on the back wall of the power supply chamber 415, and a mounting hole 4131 for mounting an oxygen connector 421 (described below) for connecting an oxygen source to the oxygen isolation chamber 413 may be arranged in the left side wall 4104 of the oxygen isolation chamber 413, so that the arrangement of the components in the casing 410 is more reasonable.

Figure 20:
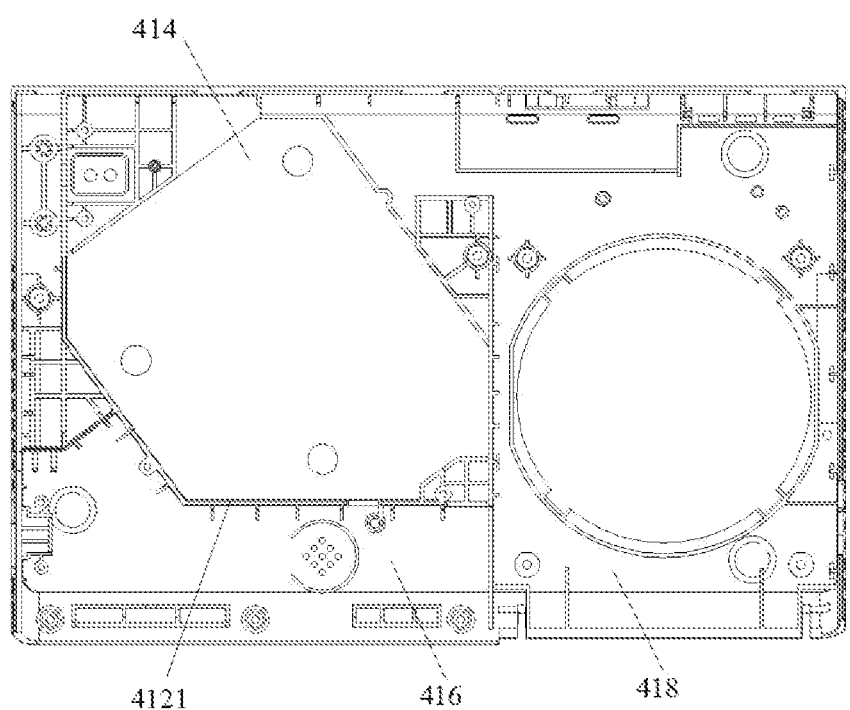
FIG. 20 is a top view of the lower partition and the lower housing in FIG. 19.

In addition, according to an embodiment of the present invention, as shown in FIGS. 18-20, the partition assembly comprises a lower partition 412 that extends upward from the bottom wall 4102 to the bottom plates 4111, is connected to the bottom plates 4111 by means of a snap-fit structure, the lower partition 412 comprises a plurality of lower side plates 4121, wherein the plurality of lower side plates 4121 are arranged in an enclosed form to define a fan chamber 414 in the lower cavity. There is not particular restriction on the specific structure of the snap-fit structure, as long as the upper partition 411 and the lower partition 412 can be detachably connected. The snap-fit structure may comprise grooves formed on the circumference of the bottom plates 4111 and flanges formed on the lower side plate 4121 and fitted with the grooves; of course, alternatively the lower side plate 4121 may be inserted into the grooves, as shown in FIG. 18.

Moreover, as shown in FIGS. 17 and 18, the casing 410 may comprise an upper casing and a lower casing, and the main unit cavity and the humidifying cavity 418 may be defined by the upper casing and the lower casing.

Figure 22:
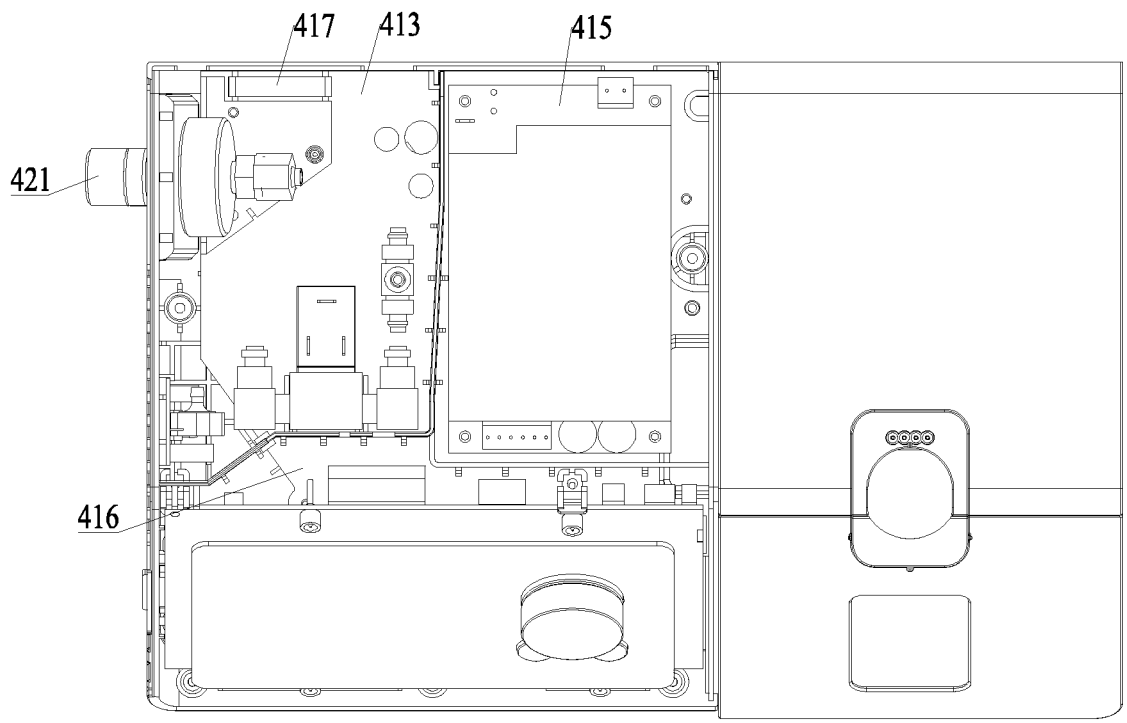
FIG. 22 is a top view of the ventilation treatment apparatus in FIG. 17, in which a partial sectional view of the main unit cavity is provided.

Since a ventilation treatment apparatus usually further comprises a main board 440 for control, the main unit cavity may further comprise a main board mounting chamber 416. According to an embodiment of the present invention, as shown in FIGS. 20 and 22, the main board mounting chamber 416 is located at the front side of the upper cavity and the lower cavity, and the casing 410 comprises a panel 4106 for defining the main unit cavity, the main board mounting chamber 416 is defined by the top wall 4101, the bottom wall 4102, the left side wall 4104, the right side wall 4105, the panel 4106, the upper side plate 4112, and the lower side plate 4121.

Figure 34:
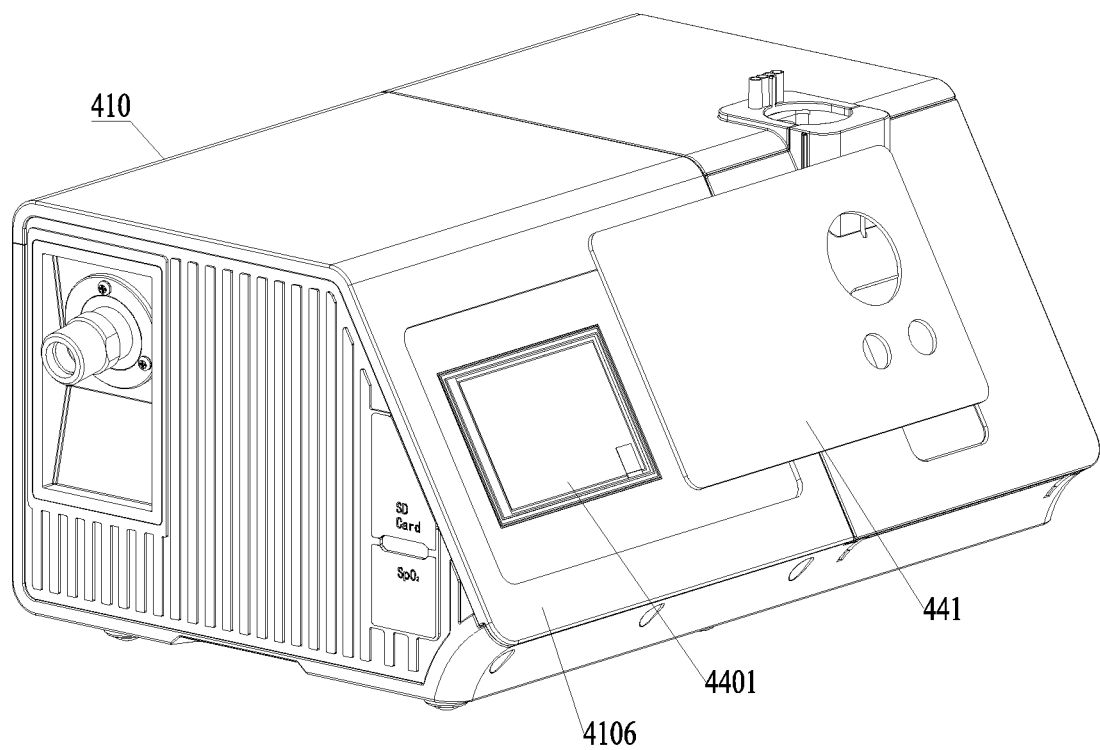
FIG. 34 is a schematic diagram of the acrylic plate in FIG. 17 before it is assembled with the panel.

As shown in FIG. 34, the main board 440 may comprise a main board screen 4401, and the panel 4106 may be provided with an opening for making room for the main board screen 4401. Moreover, knobs 444 and buttons 445 to be fitted with the control keys on the main board may be further provided on the panel 4106.

Figure 35:
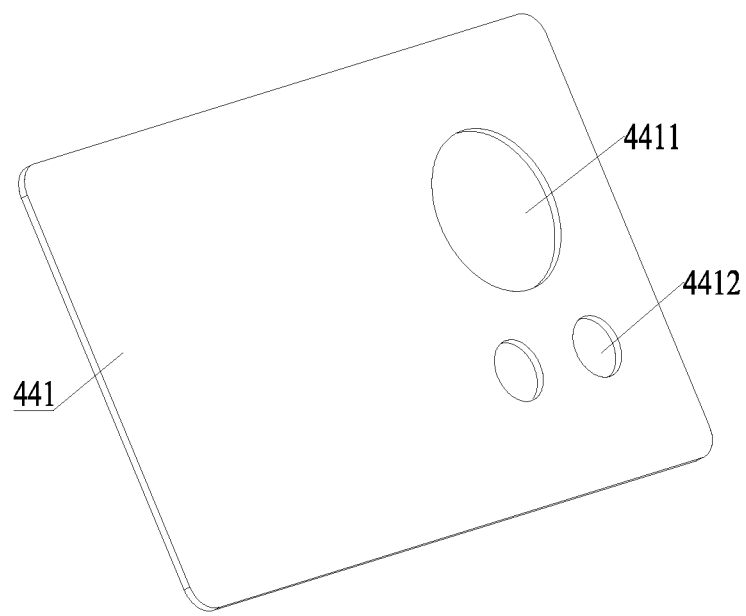
FIG. 35 is a schematic structural diagram of the acrylic plate in FIG. 34.

In order to improve the leak-tightness between the main board and the panel 4106 and prevent adverse effects on the use of the ventilation treatment apparatus resulted from invasion of external water or dust into the clearance between the main board and the panel 4106, the following embodiments may be used: (1) the sealing between the main board screen 4401 and the panel 4106 may be implemented by means of a screen bracket (e.g., a frame arranged around the main board screen 4401) made of silicone, the screen bracket can achieve positioning of the main board screen 4401 and wrap the main board screen 4401 to attain a sealing and dustproof effect against the clearance between the main board screen 4401 and the panel 4106; (2) as shown in FIG. 34, an acrylic plate 441 is provided on the panel 4106 (as shown in FIG. 35, knob mounting holes 4411 and button mounting holes 4412 may be formed in the acrylic plate 441) for covering the main board screen 4401. The acrylic plate 441 may be sealingly connected to the panel 4106 by bonding (3M adhesive may be used, owing to its excellent waterproof and bonding tightness properties), so as to prevent water or dust from invading through the clearance between the acrylic plate 441 and the panel 4106; (3) the dustproofing and waterproofing between the knobs 444, the buttons 445 and the panel 4106 may be achieved by arranging silicone pads (e.g., light guiding bases 442 and silicone button pads 446 described below) below the knobs 444 and the buttons 445; the silicone pads can seal the panel 4106 to achieve dustproofing and waterproofing, and can transfer the pressure from the knobs 444 and the buttons 445 to the control keys of main board by means of their elastic deformation so as to accomplish button pressing operations.

Figure 36:
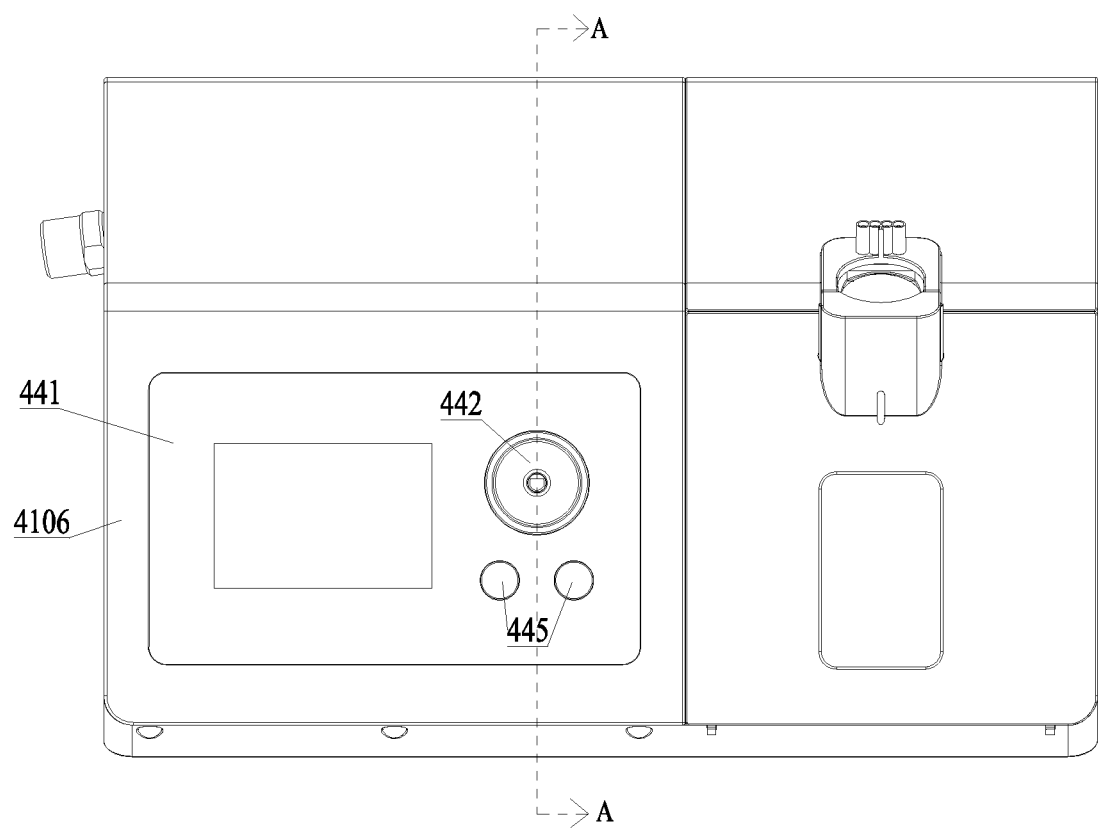
FIG. 36 is a schematic diagram of the ventilation treatment apparatus in FIG. 17 from another viewing angle, in which the knobs are omitted.
Figure 37:
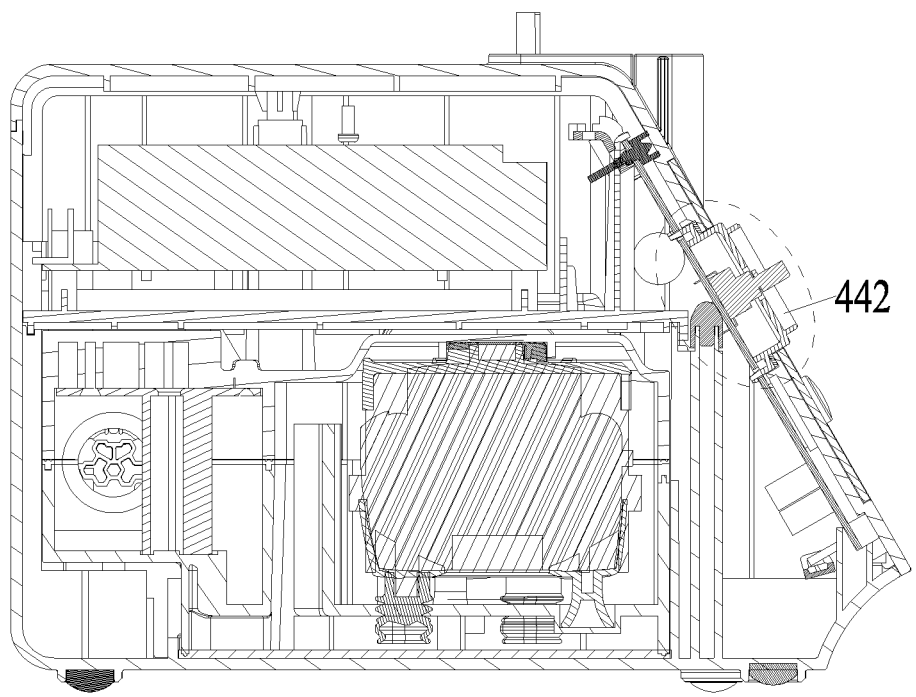
FIG. 37 is a sectional view A-A of the structure in FIG. 36.
Figure 38:
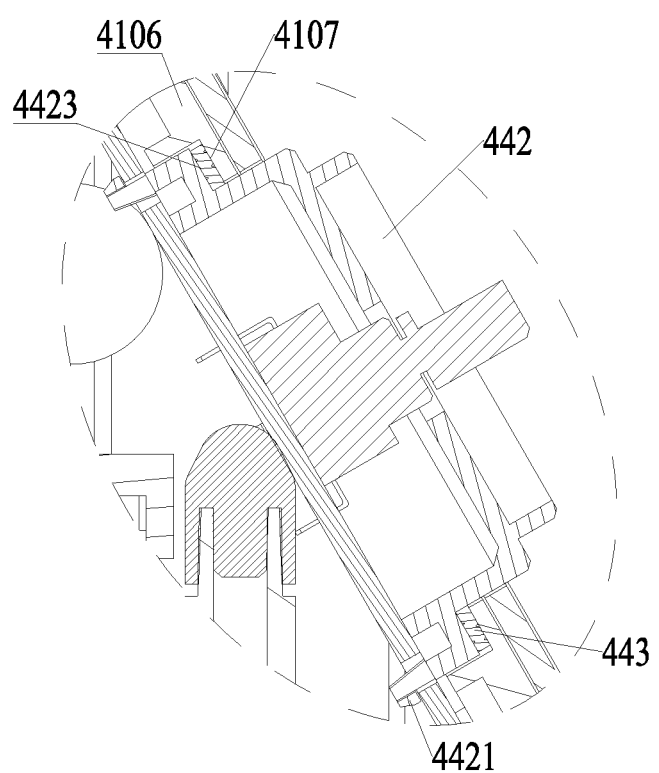
FIG. 38 is a partially enlarged view of the structure in FIG. 37.
Figure 39:
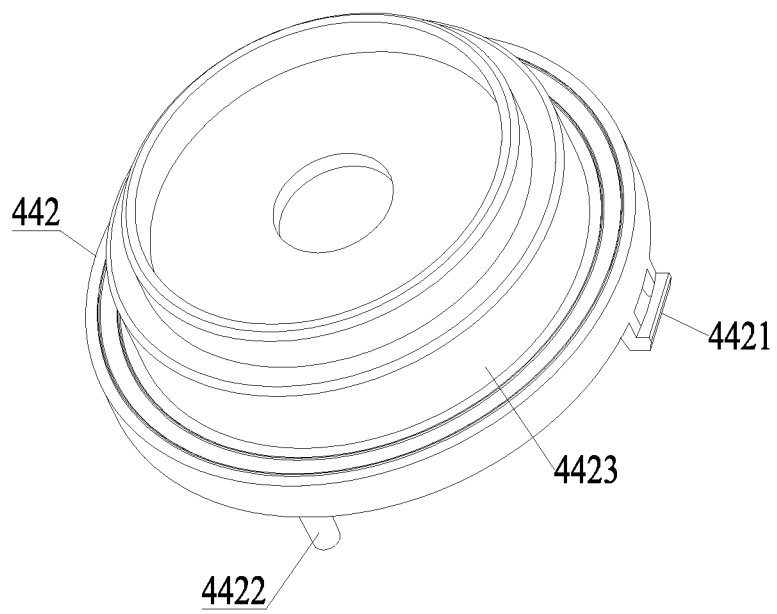
FIG. 39 is a schematic structural diagram of an embodiment of the light guiding base in the present invention.
Figure 40:
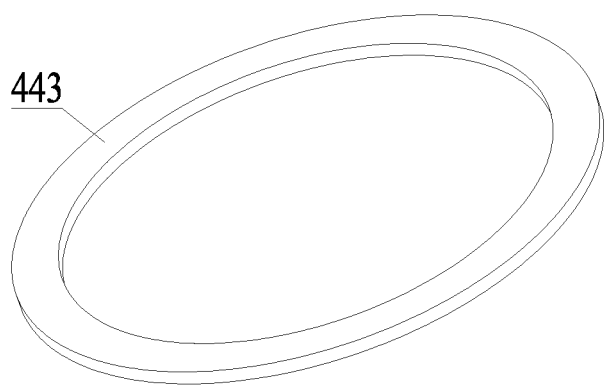
FIG. 40 is a schematic structural diagram of an embodiment of the seal ring in the present invention.
Figure 41:
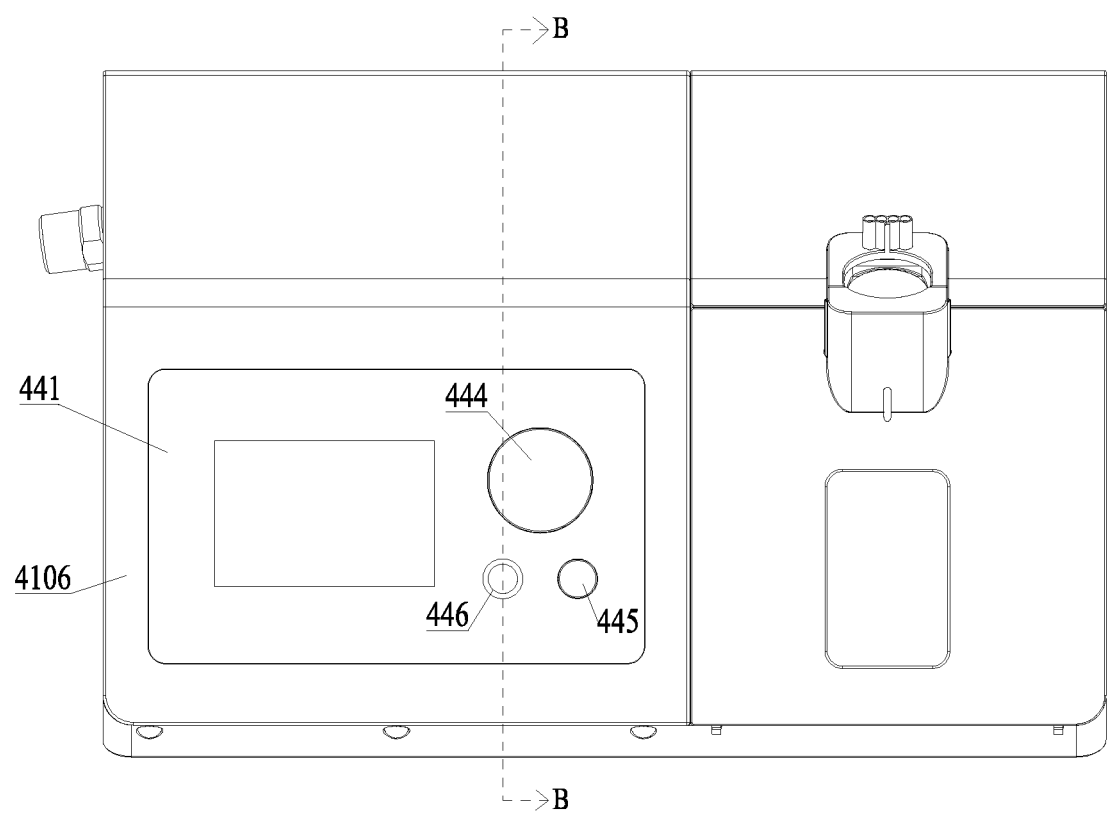
FIG. 41 is a schematic diagram of the ventilation treatment apparatus in FIG. 17 from another viewing angle, in which the buttons on the left side are omitted.
Figure 42:
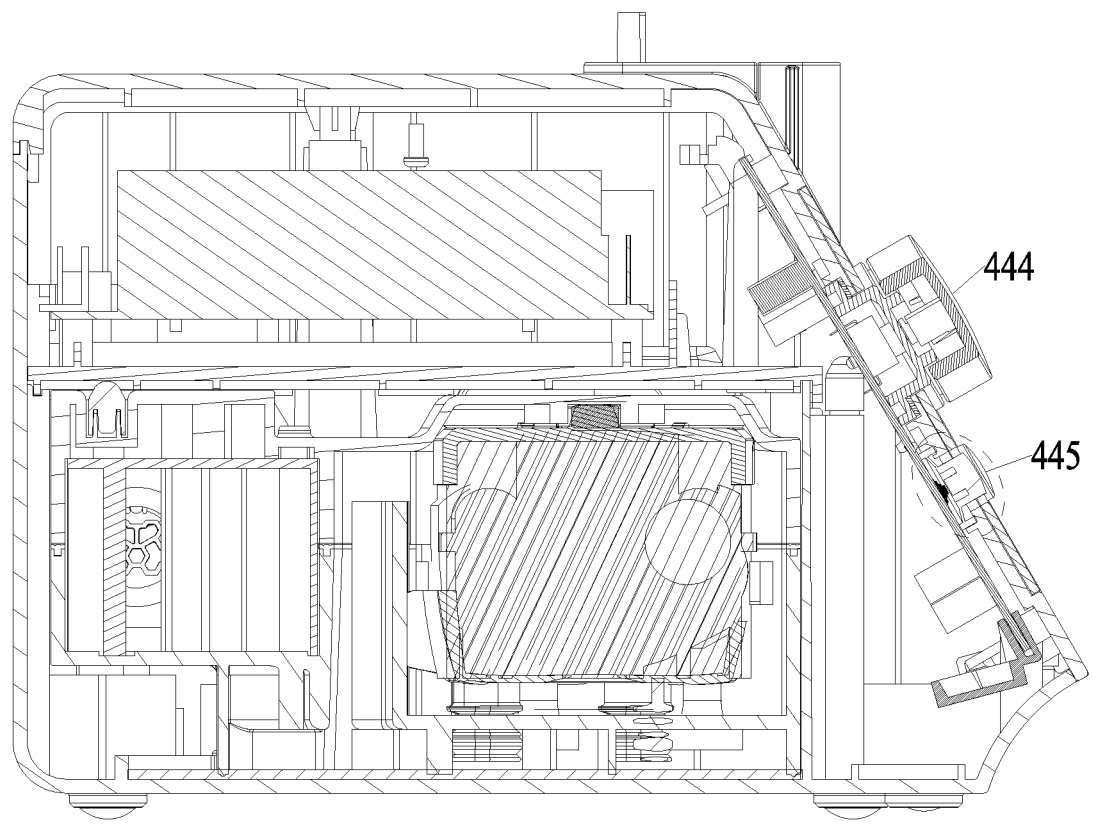
FIG. 42 is a sectional view B-B of the structure in FIG. 41.
Figure 43:
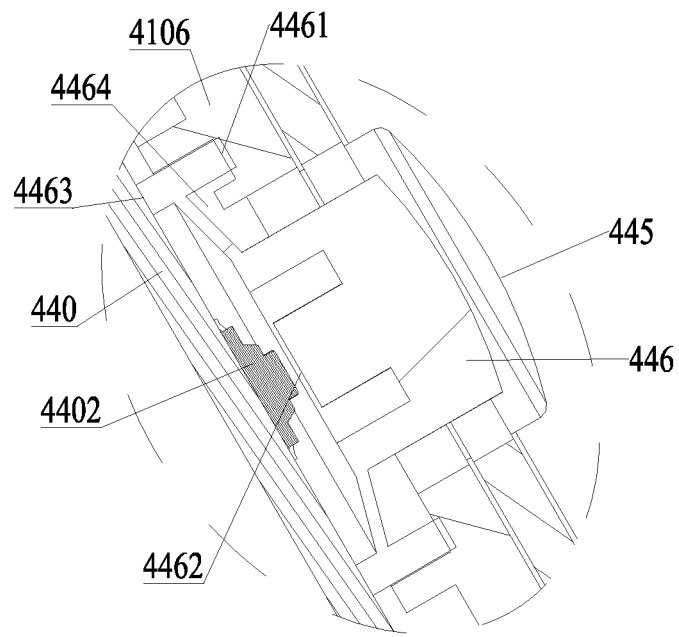
FIG. 43 is a partially enlarged view of the structure in FIG. 42.
Figure 44:
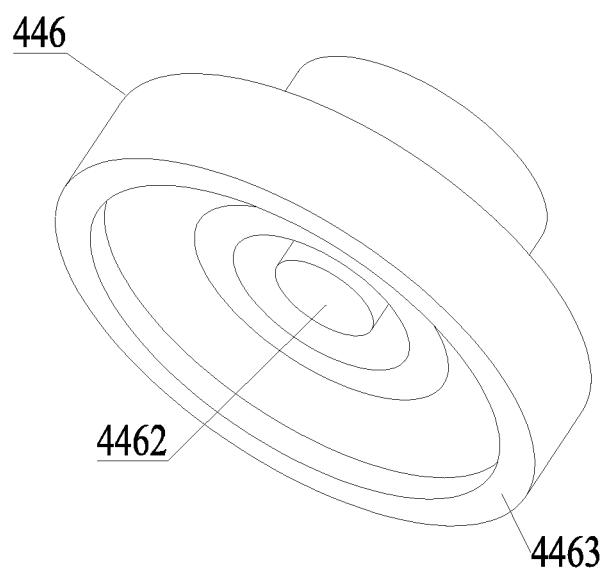
FIG. 44 is a schematic structural diagram of an embodiment of the silicone button pad in the present invention.
Figure 45:
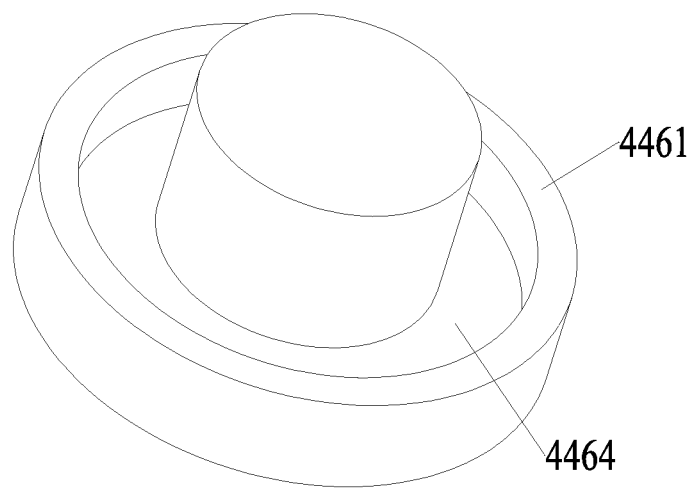
FIG. 45 is a schematic diagram of the silicone button pad in FIG. 44 from another viewing angle.

As for the dustproofing and waterproofing between the knobs 444, the buttons 445 and the panel 4106, as shown in FIG. 17, there are one knob 444 and two buttons 445 on the fan panel 4106 and the acrylic plate 441, and the knob 444 and buttons 445 finally rest on the control keys on the main board through a series of connections. In the connection process, clearance may exist, making water or dust invasion possible. To prevent that problem, as shown in FIG. 36, after the knob 444 is disassembled, a light guiding base 442 can be seen, and the bottom of the light guiding base 442 is positioned and fixedly assembled to the main board by means of a claw 4421 and a positioning post 4422. As shown in FIGS. 37-40, the light guiding base 442 has a first fitting surface 4423, the panel 4106 has a second fitting surface 4107, and there is a clearance between the first fitting surface 4423 and the second fitting surface 4107, in which a seal ring is arranged (the seal ring may be made of silicone). The clearance is eliminated under the firm squeezing action of the two fitting surfaces on the seal ring 443, and thus water or dust invasion can be prevented. In addition, as shown in FIG. 41, for the button for mute key on the left side, for example, after the button 445 is disassembled, the silicone button pad 446 can be seen, as shown in FIGS. 42-45; the bottom fitting surface 4463 of the silicone button pad 446 contacts with the main board 440; when the button 445 is pressed, the middle fitting surface 4462 of the silicone button pad 446 contacts with the control key 4402 on the main board 440 and thereby a control effect is achieved; after the silicone button pad 446 is assembled and squeezed, the top fitting surface 4461 of the silicone button pad 446 is fitted with the panel 4106 tightly, and the groove 4464 of the silicone button pad 446 contains the claw fitting surface between the button 445 and the panel; thus, even if clearance exists between the button 445 and the panel 4106, the water or dust invading through the clearance can only enter into the groove 4464, but can't further invade to the main board 440 below the panel 4106.

In the present invention, the ventilation treatment apparatus may further comprise a fan assembly 430 mounted in the fan chamber 414. The fan assembly 430 may comprise a fan housing 431 and a fan, wherein an oxygen mixing compartment 432 and a fan compartment for mounting the fan are defined in the fan housing 431, the fan housing 431 is provided with a gas inlet 4311 (it should be understood that a main gas inlet communicating with the gas inlet 4311 is arranged on the casing 410) communicating with the fan compartment and a gas outlet 4312 communicating the fan compartment and the oxygen mixing compartment 432, and an oxygen inlet 4314 and a mixed gas outlet 4315 that communicate with the oxygen mixing compartment 432. It can be understood that the gas inlet of the fan corresponds to the gas inlet 4311 of the fan compartment, and the gas outlet of the fan corresponds to the gas outlet of the fan compartment. With the above arrangement, during use, outside gas enters into the fan through the gas inlet 4311, then is discharged into the oxygen mixing compartment 432 through the gas outlet 4312, is mixed with the oxygen introduced into the oxygen mixing compartment 432 through the oxygen inlet 4314, and then the mixed gas flows out through the mixed gas outlet 4315. The discharged mixed gas can be directly conveyed to the end user, or may be conveyed to the humidifying device for warming and humidification before it is conveyed to the end user.

By arranging the oxygen mixing compartment 432 downstream of the gas outlet 4312 of the fan compartment, the oxygen will not pass through the motor of the fan; thus, the motor doesn't operate in an oxygen-enriched environment, thereby a fire risk is decreased.

Figure 25:
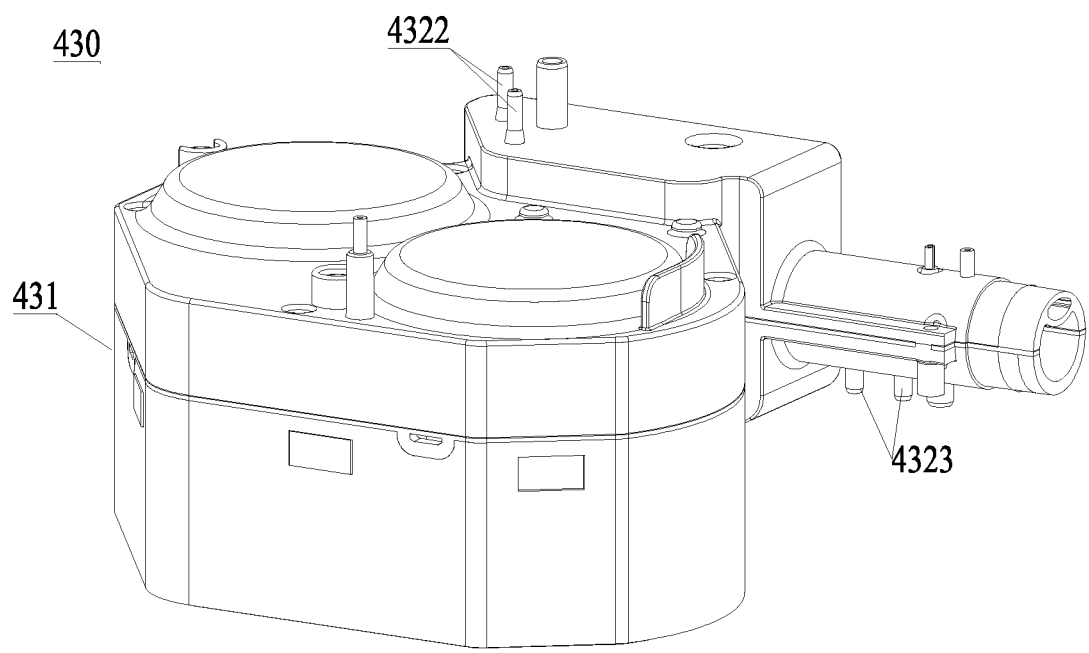
FIG. 25 is a schematic structural diagram of an embodiment of the fan assembly in the present invention.
Figure 27:
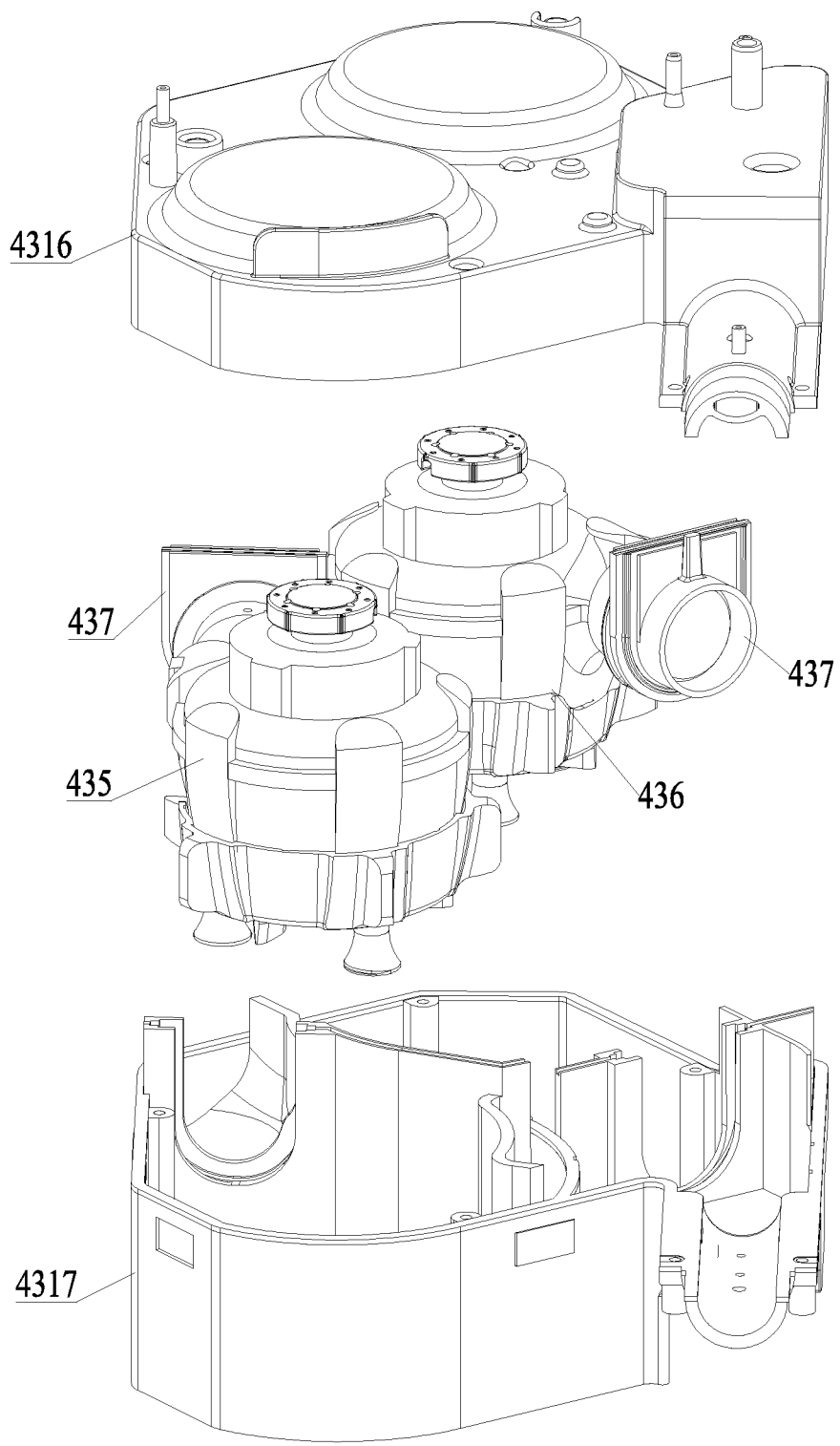
FIG. 27 is an exploded view of the fan assembly in FIG. 25.
Figure 28:
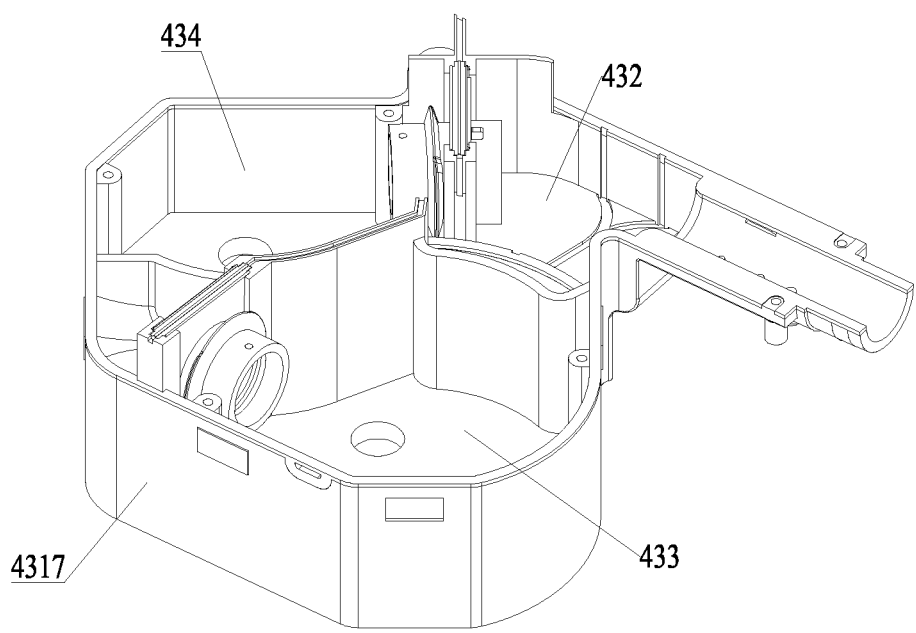
FIG. 28 is a schematic diagram of the assembling of the lower fan housing and the connecting tube in FIG. 26.
Figure 29:
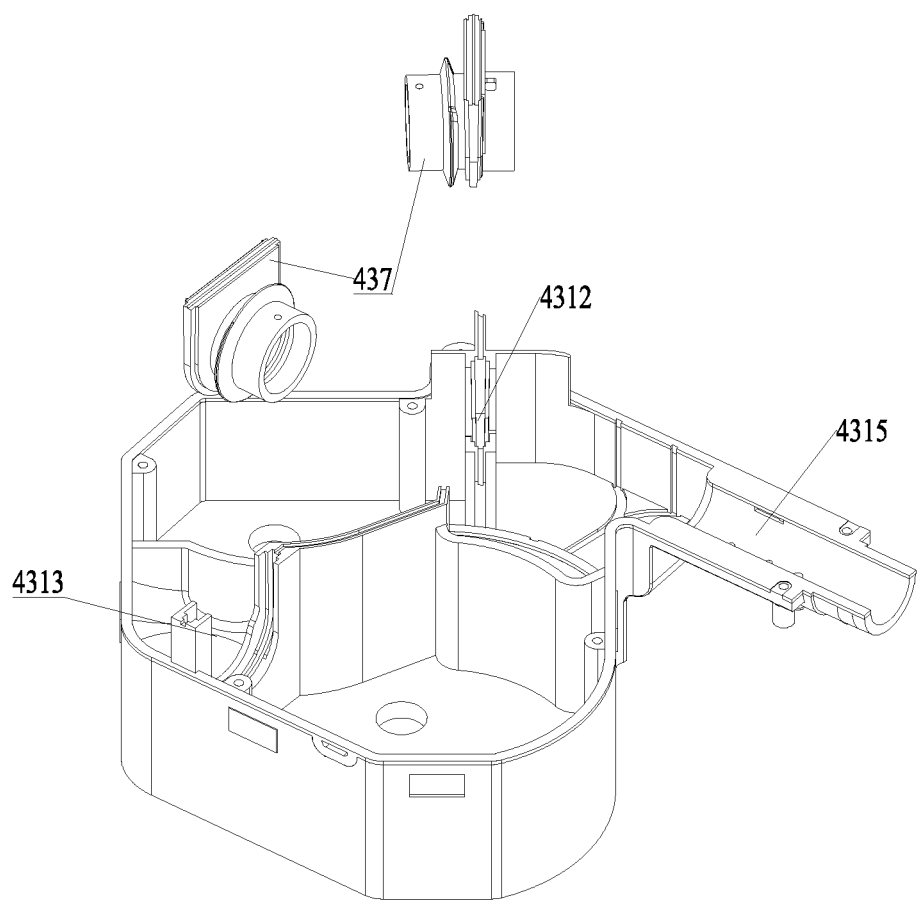
FIG. 29 is an exploded view of the structure in FIG. 28.

Specifically, for example, in an embodiment shown in FIGS. 25 and 27, the fan assembly 430 comprises a fan housing 431, a first fan 435 and a second fan 436, wherein the fan housing 431 comprises a first fan housing and a second fan housing, which are connected in series; an oxygen mixing compartment 432, a first fan compartment 433 for mounting the first fan 435, and a second fan compartment 434 for mounting the second fan 436 are defined in the fan housing 431; the fan housing 431 is provided with a gas inlet 4311 communicating with the first fan compartment 433, a communicating port 4313 communicating the first fan compartment 433 and the second fan compartment 434, and a gas outlet 4312 communicating the second fan compartment 434 and the oxygen mixing compartment 432. The gas inlet of the first fan 435 corresponds to the gas inlet 4311, the gas outlet of the first fan 435 and the gas inlet of the second fan 436 correspond to the communicating port 4313, and the gas outlet of the second fan 436 corresponds to the gas outlet 4312. In addition, as shown in FIGS. 27-29, connecting tubes 437 may be provided at the communication port 4313 and the gas outlet 4312 respectively, the connecting tube 437 located at the communication port 4313 is configured to connect the gas outlet of the first fan 435 and the gas inlet of the second fan 436 and ensure the airtightness of the first fan compartment 433 and the second fan compartment 434 at the same time; the connecting tube 437 located at the gas outlet 4312 is configured to connect the gas outlet of the second fan 436 and ensure the airtightness of the second fan compartment 434 and the oxygen mixing compartment 432 at the same time. The connecting tubes 437 are preferably silicone hoses.

In the present invention, as shown in FIGS. 25, 27 and 30-31, the fan housing 431 may comprise an upper fan housing 4316 and a lower fan housing 4317, and the fan compartment and oxygen mixing compartment 432 are defined by the upper fan housing 4316 and the lower fan housing 4317. The oxygen inlet 4314 may be provided on the upper fan housing 4316.

Figure 30:
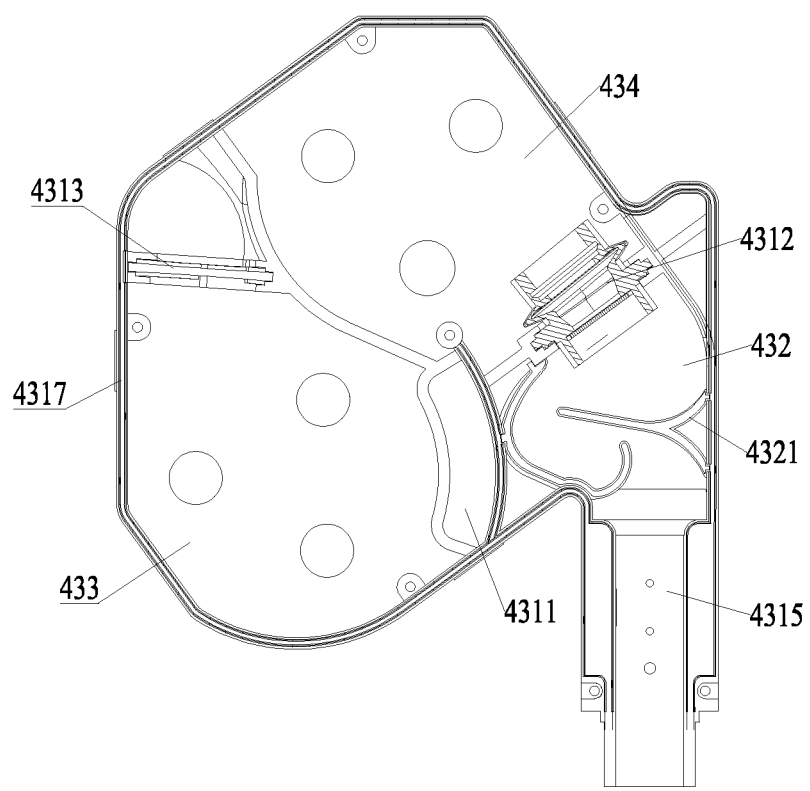
FIG. 30 is a schematic cross-sectional view of the lower fan housing in FIG. 27.
Figure 31:
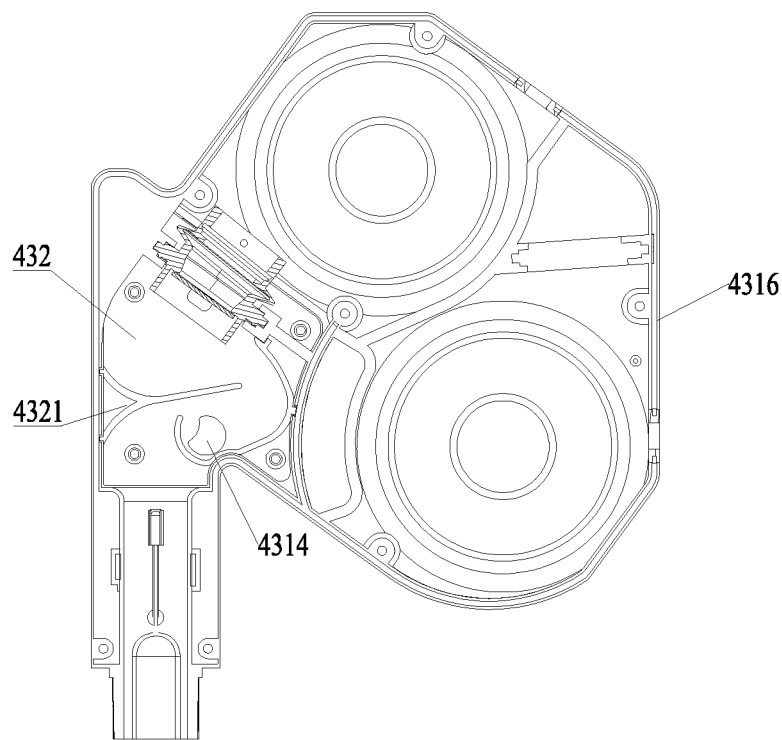
FIG. 31 is a schematic cross-sectional view of the upper fan housing in FIG. 27.

Moreover, in an embodiment of the present invention, as shown in FIGS. 25, 30 and 31, the fan assembly 430 may comprise a baffle 4321 disposed in the oxygen mixing compartment 432 for mixing the gas and guiding the gas flow, a first measuring component 4322 for measuring the oxygen flow at the oxygen inlet 4314 and a second measuring component 4323 for measuring the oxygen concentration at the mixed gas outlet 4315. The baffle 4321 can improve the uniformity of gas mixing and has a guiding effect on the mixed gas flow, and may have any appropriate structure (for example, as shown in FIGS. 30 and 31). There is no particular restriction on the structure of the baffle 4321.

Figure 26:
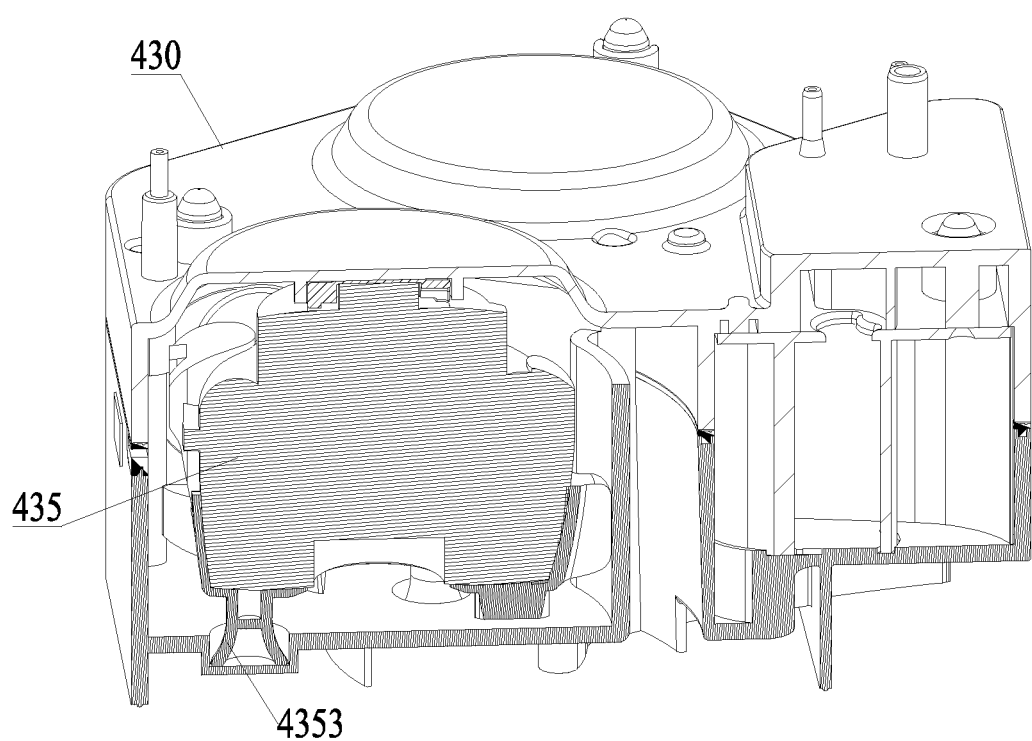
FIG. 26 is a vertical sectional view of the fan assembly in FIG. 25.
Figure 32:
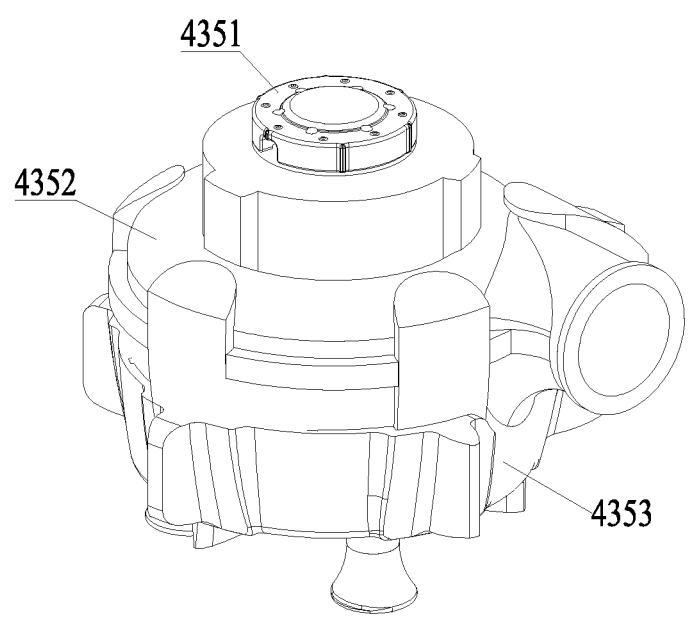
FIG. 32 is a schematic structural diagram of an embodiment of the fan in the present invention.
Figure 33:
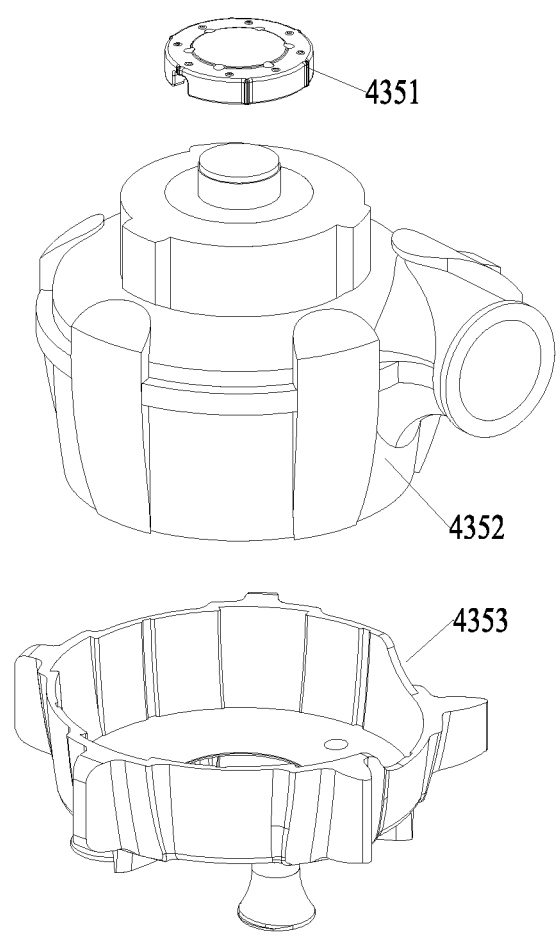
FIG. 33 is an exploded view of the fan in FIG. 32.

In the present invention, as shown in FIGS. 32 and 33, the fans (e.g., the first fan 435 and the second fan 436, which is to say, the first fan 435 and the second fan 436 may have the same structure) may comprise a positioning ring 4351, a main body 4352 and a supporting component 4353 respectively. The main body 4352 is mounted together with the upper positioning ring 4351 and the lower supporting component 4353 as an integral piece in the fan compartment. As shown in FIG. 26, the positioning ring 4351 may be fitted with the top wall of the fan compartment, and three legs of the supporting component 4353 may be fitted with the bottom wall of the fan compartment and attain a shock absorption effect. The positioning ring 4351 and the supporting component 4353 are preferably flexible components, such as silicone rubber components.

Figure 23:
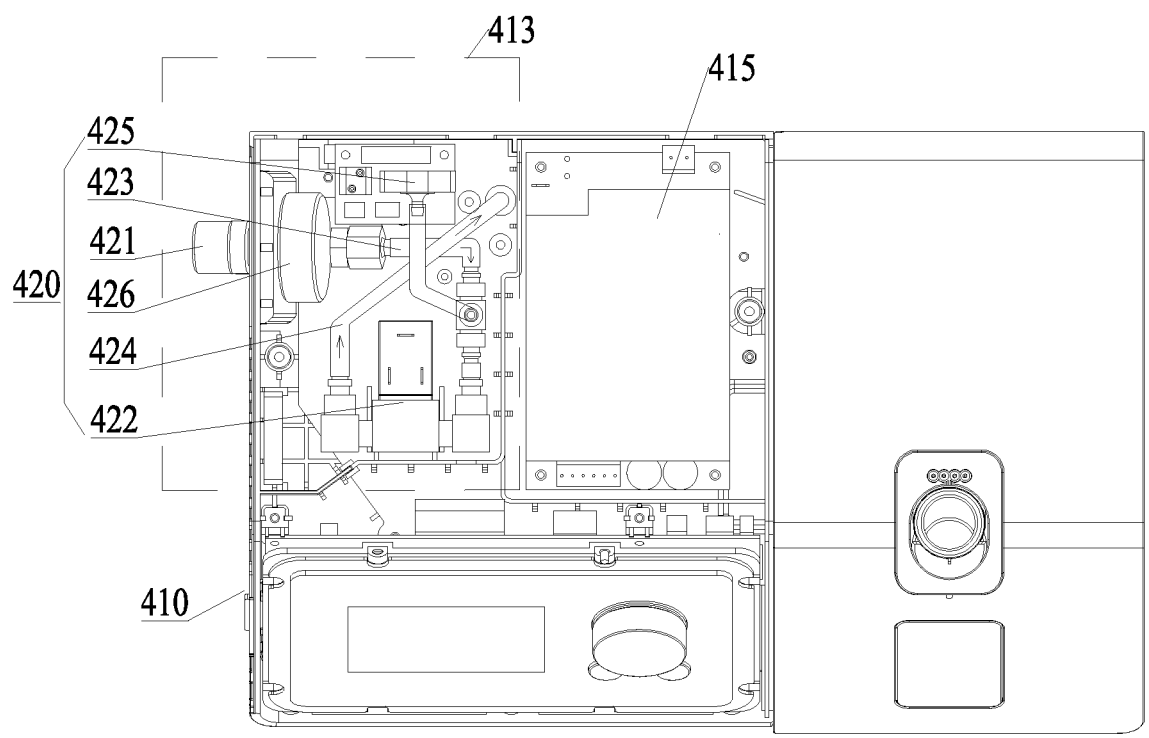
FIG. 23 is a top view of the ventilation treatment apparatus in FIG. 17, in which a partial sectional view of the main unit cavity is provided.

In the present invention, the oxygen assembly 420 refers to a component related with oxygen. According to an embodiment of the present invention, as shown in FIG. 23, the oxygen assembly 420 comprises an oxygen connector 421, an oxygen proportioning valve 422, a first tube 423 and a second tube 424, a first tube 423 communicating with the oxygen connector 421 and the oxygen proportioning valve 422, and a second tube 424 communicating with the oxygen proportioning valve 422 and the oxygen inlet 4314. During use, oxygen enters into the oxygen isolation chamber 413 via the oxygen connector 421, and then enters into the oxygen proportioning valve 422 through the first tube 423, the flow of the oxygen is regulated by the oxygen proportioning valve 422 (to a low flow), then the oxygen is charged into the oxygen mixing compartment 432 through the second tube 424 via the oxygen inlet 4314. In case there is any leakage at the joints between the oxygen connector 421, the oxygen proportioning valve 422, the first tube 423 and the second tube 424, the leaking oxygen will not invade into other areas of the main unit cavity since these components are enclosed in the oxygen isolation chamber 413.

The oxygen assembly 420 may further comprise an oxygen pressure sensor 425, which is used to measure the pressure in the first tube 423, i.e., measure the pressure of the high-pressure oxygen connected into the ventilation treatment apparatus. Thus, by detecting the pressure of the oxygen entering into the ventilation treatment apparatus, accidental oxygen interruption can be detected and an alarm can be provided. Moreover, by measuring the pressure of the oxygen, compensation may be made when the oxygen concentration of the mixed gas is calculated.

Figure 24:
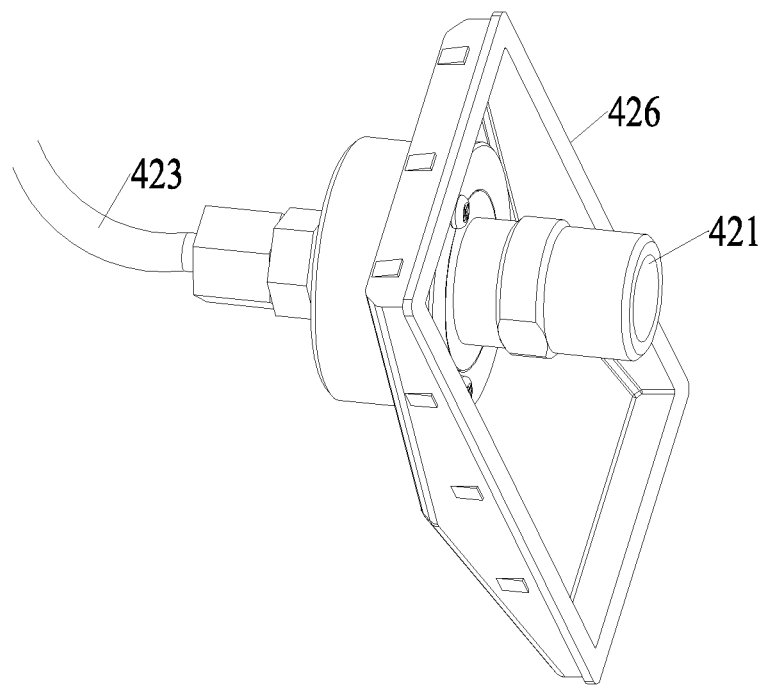
FIG. 24 is a schematic assembly diagram of the oxygen connector, the bracket, and the first tube in the present invention.

In addition, as shown in FIGS. 23 and 24, the oxygen assembly 420 may further comprise a bracket 426, and the oxygen connector 421 may be mounted at the mounting hole 4131 in the left side wall 4104 and fixed to the left side wall 4104 of the casing 410 by means of the bracket 426.

In the present invention, as shown in FIG. 22, a ventilating fan 417 may be provided in the oxygen isolation chamber 413. In case of oxygen leakage, the oxygen can be vented quickly by means of the ventilating fan 417, so as to decrease the oxygen concentration.

While some preferred embodiments of the present invention are described above with reference to the accompanying drawings, the present invention is not limited to the details in those embodiments. Those skilled in the art can make modifications and variations to the technical scheme of the present invention, without departing from the spirit of the present invention. However, all these modifications and variations shall be deemed as falling into the scope of protection of the present invention.

In addition, it should be noted that the specific technical features described in above embodiments may be combined in any appropriate form, provided that there is no conflict. To avoid unnecessary repetition, the possible combinations are not described specifically in the present invention.

Moreover, different embodiments of the present invention may also be combined freely as required, as long as the combinations don't deviate from the ideal and spirit of the present invention. However, such combinations shall also be deemed as falling into the scope disclosed in the present invention.

The invention claimed is:

1. A structure for mounting a water tank on a ventilation treatment apparatus, comprising:
a cavity for containing a water tank; and
a side wall that defines the cavity, wherein the side wall comprises:
a two-layer structure that includes an inner side wall and an outer side wall spaced apart from each other,
a first gas hole is provided in the inner side wall, and
a second gas hole is provided in the outer side wall, wherein the first gas hole and the second gas hole are arranged in a staggered manner in a direction perpendicular to the side wall, the inner side wall is parallel to the outer side wall; and/or the structure further comprises a guide channel arranged on a bottom of the side wall for guiding out water between the outer side wall and the inner side wall; and a bottom plate extending inward from a bottom end of the outer side wall and a stop rib spaced apart from the outer side wall and extending upward from the bottom plate, the stop rib is located on an inner side of the inner side wall, and the guide channel is defined by the outer side wall, the bottom plate, and the stop rib; or a bottom plate connected between the outer side wall and the inner side wall, and the guide channel is defined by the outer side wall, the inner side wall and the bottom plate, wherein the bottom plate is provided with a drain port.

2. The structure according to claim 1, wherein:
the first gas hole includes a plurality of first gas holes that are spaced apart from each other in a height direction of the inner side wall and arranged in rows in a width direction of the inner side wall; and/or
the second gas hole includes a plurality of second gas holes that are spaced apart from each other in the height direction of the outer side wall, and arranged in rows in the width direction of the outer side wall.

3. The structure according to claim 1, further comprising:
a top wall for defining the cavity, wherein the top wall comprises an inner top wall and an outer top wall that are spaced apart from each other.

4. The structure according to claim 3, further comprising:
an LED lamp that is provided on the inner top wall, and/or
a wiring groove is provided in a top surface of the inner top wall.

5. The structure according to any of claim 1, further comprising:
a bottom wall for defining the cavity, a base arranged below the bottom wall, and a heating plate, wherein the bottom wall is provided with an opening for containing the heating plate, and the base is provided with a supporting component for supporting the heating plate at the opening; and/or
a back wall for defining the cavity, with an opening for mounting an intake tube of the ventilation treatment apparatus is arranged in the back wall, and a guiding channel for guiding the water tank to the cavity in a way that a gas inlet of the water tank is aligned to the opening.

6. The structure according to claim 5, further comprising
a main body and an adapter connected above the main body, wherein the adapter comprises a horizontal tube extending in a horizontal assembling direction of the water tank, and an end of the horizontal tube oriented to the back wall is the gas inlet.

7. The structure according to claim 6, wherein the guiding channel comprises:
a first guide that is fitted with the horizontal tube to guide the assembling of the water tank and/or
a second guide that is fitted with the main body to guide the assembling of the water tank.

8. The structure according to claim 7, further comprising
a top wall for defining the cavity, the first guide comprises two guiding plates protruding downward from the top wall and extending in an assembling direction, the two guiding plates are located at two sides of the opening in a spaced manner in a direction perpendicular to the assembling direction, and the horizontal tube is able to enter into the spacing between the two guiding plates; and/or
two side walls arranged opposite to each other, the second guide comprises two guide rails arranged on the two side walls respectively, and the main body is provided with a sliding part that is able to be fitted with the two guide rails and slide along the two guide rails.

9. The structure according to claim 8, wherein:
a guiding bevel is formed on an end of at least one of the two guiding plates away from the opening.

10. The structure according to claim 9, further comprising:
a flange arranged on one of an inner side of at one of the two guiding plates and an outer wall of the horizontal tube, and
a groove arranged on the other of the inner side of at least one of the two guiding plates and the outer wall of the horizontal tube to be fitted with the flange.

11. The structure according to claim 8, wherein;
a cross section of the main body is circular, the sliding part is an annular convex edge protruding outward from an outer circumferential surface of the main body and extending in a circumferential direction of the main body, the guide rails comprise two guiding ribs that protrude from an inner surface of the side wall and extend in an assembling direction, and the two guiding ribs have an interval in a height direction of the side wall, and the interval is set to allow the annular convex edge to enter; and/or
the spacing between the two guide rails is decreased in the assembling direction to prevent the main body to move further in the assembling direction after it reaches an assembling position.

12. An apparatus for providing a ventilation treatment, comprising a main unit, the water tank, and the structure according to claim 1, wherein the structure is arranged on the main unit.

13. The apparatus according to claim 12, comprising a casing and an oxygen assembly, wherein a main unit cavity is defined in the casing, a partition assembly is arranged in the main unit cavity and configured to separate an airtight oxygen isolation chamber in the main unit cavity, and the oxygen assembly is mounted in the airtight oxygen isolation chamber.

14. The apparatus according to claim 13, wherein:
the partition assembly is configured to separate a fan chamber in the main unit cavity, the casing comprises a top wall and a bottom wall for defining the main unit cavity,
the partition assembly comprises an upper partition that comprises bottom plates arranged above the bottom wall in a spaced manner,
the bottom plates separate the main unit cavity into an upper cavity and a lower cavity, the airtight oxygen isolation chamber is located in the upper cavity, and the fan chamber is located in the lower cavity.

15. The apparatus according to claim 14, wherein:
a power supply chamber is arranged in the main unit cavity, the partition assembly further comprises an upper side plate that extends from the bottom plates upward to the top wall and separates the upper cavity into a left cavity and a right cavity, and the airtight oxygen isolation chamber and the power supply chamber are located in either of the left cavity and the right cavity respectively; and/or
the partition assembly comprises a lower partition that extends from the bottom wall upward to the bottom plates and is connected to the bottom plates by means of a snap-fit structure, and the lower partition comprises a plurality of lower side plates that enclose with each other to define the fan chamber in the lower cavity.

16. The apparatus according to claim 14, further comprising:
a fan assembly that is mounted in the fan chamber, the fan assembly comprises a fan housing and a fan, wherein an oxygen mixing compartment and a fan compartment for mounting the fan are defined in the fan housing, the fan housing is provided with a gas inlet communicating with the fan compartment and a gas outlet communicating with the fan compartment and the oxygen mixing compartment, and the fan housing is further provided an oxygen inlet and a mixed gas outlet that communicate with the oxygen mixing compartment.

17. The apparatus according to claim 16, wherein the fan assembly comprises a baffle arranged in the oxygen mixing compartment and configured to mix a gas and guide the gas to flow, a first sensor that measures an oxygen flow at the oxygen inlet, and a second sensor that measures an oxygen concentration at the mixed gas outlet; and/or the oxygen assembly comprises an oxygen connector, an oxygen proportioning valve, a first tube and a second tube, wherein the first tube communicates with the oxygen connector and the oxygen proportioning valve, and the second tube communicates with the oxygen proportioning valve and the oxygen inlet.

18. The apparatus according to claim 13, wherein a ventilating fan is provided in the airtight oxygen isolation chamber.

\* \* \* \* \*